US012620483B2

(12) United States Patent
Gray et al.

(10) Patent No.: US 12,620,483 B2
(45) Date of Patent: May 5, 2026

(54) SYSTEMS AND METHODS FOR CONTRAST IMAGING

(71) Applicant: GE Precision Healthcare LLC, Waukesha, WI (US)

(72) Inventors: Benjamin Gray, Wauwatosa, WI (US); Aurelie Ribet Le Deley, Brookkfield, WI (US); Adwait Cheoolkar, Waukesha, WI (US); Timothy Voiles, Oconomowoc, WI (US); Nick Heil, Mosinee, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 423 days.

(21) Appl. No.: 18/499,043

(22) Filed: Oct. 31, 2023

(65) Prior Publication Data

US 2025/0140395 A1     May 1, 2025

(51) Int. Cl.
*G01R 33/56* (2006.01)
*G16H 40/63* (2018.01)

(52) U.S. Cl.
CPC ......... *G16H 40/63* (2018.01); *G01R 33/5601* (2013.01); *G01R 33/5608* (2013.01)

(58) Field of Classification Search
CPC ................ G16H 40/63; G01R 33/5601; G01R 33/5608; G01R 33/546
See application file for complete search history.

(56) References Cited

U.S. PATENT DOCUMENTS 6,167,293 A * 12/2000 Chenevert ............ G01R 33/563
324/309
2008/0114234 A1* 5/2008 Gering ............. G01R 33/56366
600/411

OTHER PUBLICATIONS

Gray, B. et al., "Systems and Methods for Contrast Imaging," U.S. Appl. No. 18/499,055, filed Oct. 31, 2023, 76 pages.

* cited by examiner

*Primary Examiner* — G.M. A Hyder
(74) *Attorney, Agent, or Firm* — McCoy Russell LLP

(57) ABSTRACT

Systems and methods are provided for contrast scans. In one example, a computing device is configured to display a scan interface in a prescription view on a screen and to receive user input of a contrast observation slice for tracking arrival of a contrast bolus during a contrast scan. The screen is further configured to display a scanning button that can be reached directly from the scan interface, the scanning button selectable to launch a live scanning view of the scan interface that enables live 2D images of the contrast observation slice to seen within the scan interface. The live scanning view includes a contrast tracking display panel that displays an auto-triggering button that is selectable to enable auto-triggering of post-contrast image acquisition and that displays a contrast intensity plot determined from the live 2D images.

20 Claims, 15 Drawing Sheets

SYSTEMS AND METHODS FOR CONTRAST IMAGING

TECHNICAL FIELD

The present description relates generally to medical imaging. More specifically, the present disclosure relates to contrast-enhanced magnetic resonance imaging.

BACKGROUND

Magnetic resonance imaging (MRI) is a medical imaging modality that can create images of the inside of a human body without using x-rays or other ionizing radiation. An MRI scan typically includes a series of radiofrequency (RF) excitation pulses and magnetic field gradient pulses that are played out with specific timings and in a specific sequence to prepare contrast and encode spatial information into the signal to generate an image. To enhance certain anatomical features, some MRI scans may include the administration of a contrast agent to a subject being imaged.

BRIEF DESCRIPTION

In one example, a computing device comprises a display screen, the computing device being configured to display on the screen a scan interface in a prescription view, and further configured to receive user input via the scan interface in the prescription view to enable prescription of a contrast observation slice for tracking arrival of a contrast bolus during a contrast scan, and additionally being configured to display on the screen a scanning button that can be reached directly from the scan interface in the prescription view, wherein the scanning button is selectable to launch a live scanning view of the scan interface that enables live 2D images of the contrast observation slice to seen within the scan interface, the live scanning view further including a contrast tracking display panel that displays an auto-triggering button that is selectable to enable auto-triggering of post-contrast image acquisition and enable a contrast intensity plot determined from the live 2D images to be seen within the contrast tracking display panel.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
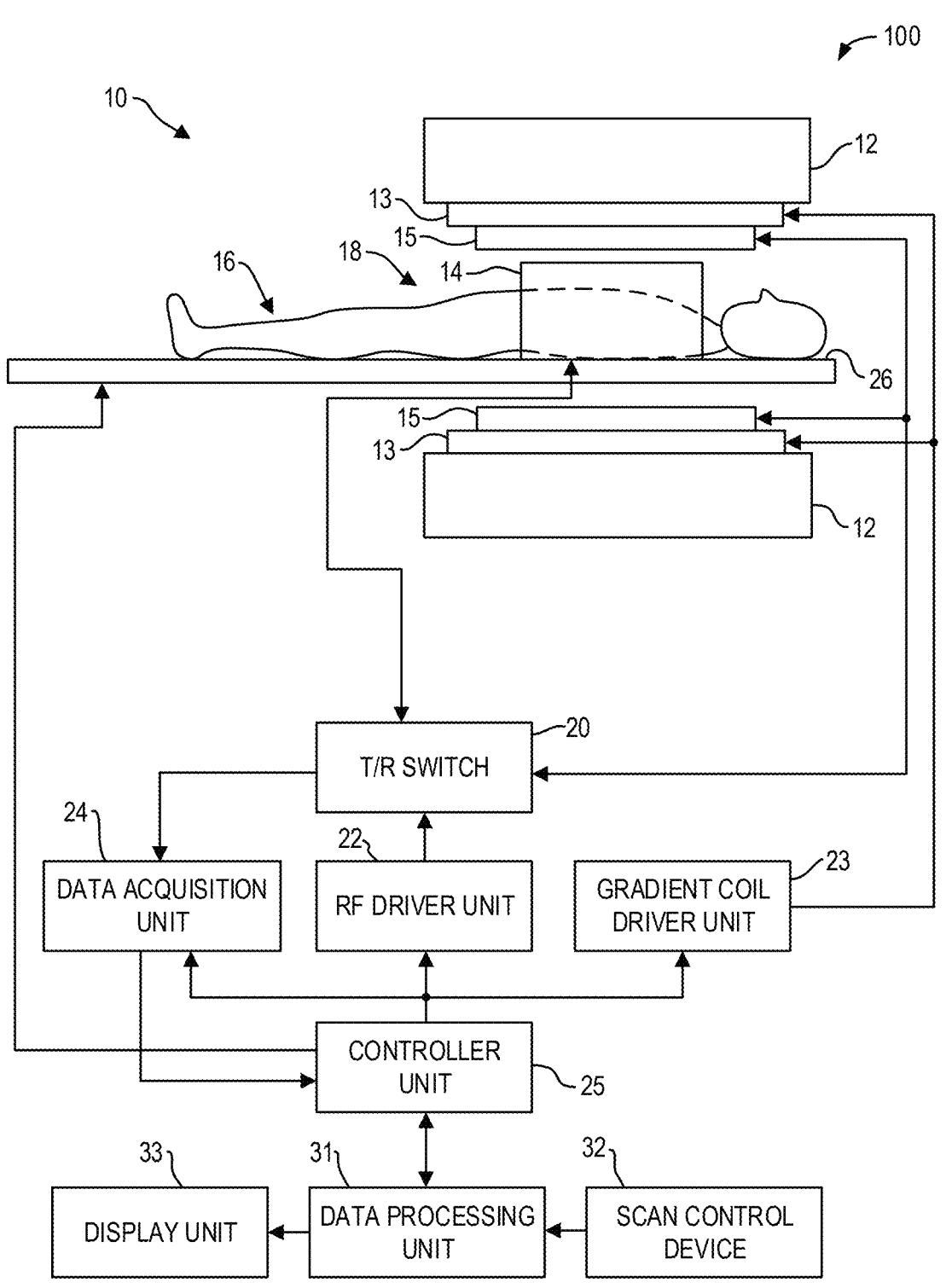
FIG. 1 is a block diagram of an MRI apparatus according to an embodiment of the disclosure.

The following description relates to medical imaging workflows, and in particular contrast-enhanced magnetic resonance (MR) workflows. Contrast-enhanced MR imaging (MRI) scans include the administration of a paramagnetic contrast agent, such as gadolinium-based contrast agents, to an imaging subject in order to enhance contrast of various tissues of the imaging subject. Contrast-enhanced MRI scans demand that imaging start at the beginning or peak level of contrast enhancement in a region of interest (such as an artery). A typical workflow for a contrast-enhanced MRI scan includes an estimation of the time for a contrast bolus of the contrast agent to travel from the injection site to the region of interest (ROI) and the acquisition is started by an operator of the MRI system in the hopes that the operator has the timing correct. To estimate the time from when the contrast bolus is injected to when the contrast bolus arrives at the ROI, low-resolution live 2D images of the ROI may be displayed, and the operator may trigger the start of the post-contrast acquisitions (which may include acquisitions in order to generate higher resolution, 3D images) based on the viewed contrast intensity of the ROI via the live 2D images. In other examples, the MRI system may track/plot the contrast intensity of the ROI over time and the MRI system or the operator may trigger the start of the post-contrast acquisitions based on the plot reaching a threshold value.

However, each of these approaches has drawbacks. For example, some imaging subjects may never exhibit a contrast level in the ROI that is high enough to reach the threshold for triggering the start of the post-contrast acquisitions. Further, relying solely on the live 2D images may result in inadvertent timing errors (e.g., delays) in triggering the post-contrast acquisitions due to operator distractions or misinterpretation of the contrast level in the live 2D images. Thus, it may be desirable for the operator of the MRI system to be able to view both the contrast plot and the live 2D images to make an informed decision, and it may be further desirable for the MRI system to provide a back-up timing for automatically triggering the start of the post-contrast acquisitions to avoid missed scans due to unusual contrast kinetics of the imaging subject, for example. With current MRI systems, the live 2D images and contrast plot are not be displayed simultaneously, and monitoring both the live 2D images and the contrast plot may demand the operator switch between different interfaces or toggle between different views, which may further exacerbate the issues mentioned above by increasing the cognitive load placed on the operator and increasing the likelihood the operator may be become distracted, which may increase the likelihood that the correct timing for initiating the contrast scan acquisitions will be missed.

Thus, according to embodiments disclosed herein, a scan interface may be displayed that gives the operator of the MRI system a real-time, live view of the contrast scan process by allowing the operator to visualize the arrival of the contrast bolus via both live 2D images and an automatically-generated, live contrast plot that are displayed simultaneously in one interface, combined with multiple methods of triggering the contrast scan acquisitions, including an operator-initiated trigger and an auto/system-initiated trigger, each of which may include a back-up trigger based on a time since injection of the contrast bolus. The scan interface may further allow a scan prescription for the contrast scan to be set via an easy-to-visualize timeline, as well as allow operator adjustments to the ROI for triggering the post-contrast scan and other parameters. These functionalities may be presented on a single interface displayed on a display associated with a computing device (e.g., a scan control device), which may provide a specific manner of displaying a limited set of information (e.g., the live 2D images, contrast plot, scan prescription timeline, and/or various user interface controls selectable to adjust scan parameters) to the user, rather than using conventional user interface methods to display a generic index/list on a computer that may require the user to step through multiple menus and/or interfaces of images, plots, and scan prescription information to find the relevant contrast level information and scan prescription settings. The scan interface disclosed herein may be advantageous because it avoids a user having to scroll around and switch views/interfaces multiple times to find desired data/functionality, thereby preventing drilling down through many layers to get the desired data/functionality which may be slow, complex, and difficult to learn. The disclosed scan interface may improve the efficiency of using the computing device by bringing together the scan information most relevant to the user, allowing the user to view the most relevant scan information without accessing separate interfaces, menus, or display panels where contrast level information and scan prescription settings may be displayed. The speed of a user's navigation through various views and windows may be improved because the disclosed scan interface saves the user from navigating to separate interfaces or display panels to enable the contrast level or scan prescription settings to be seen or a function of interest to be activated.

Figure 4:
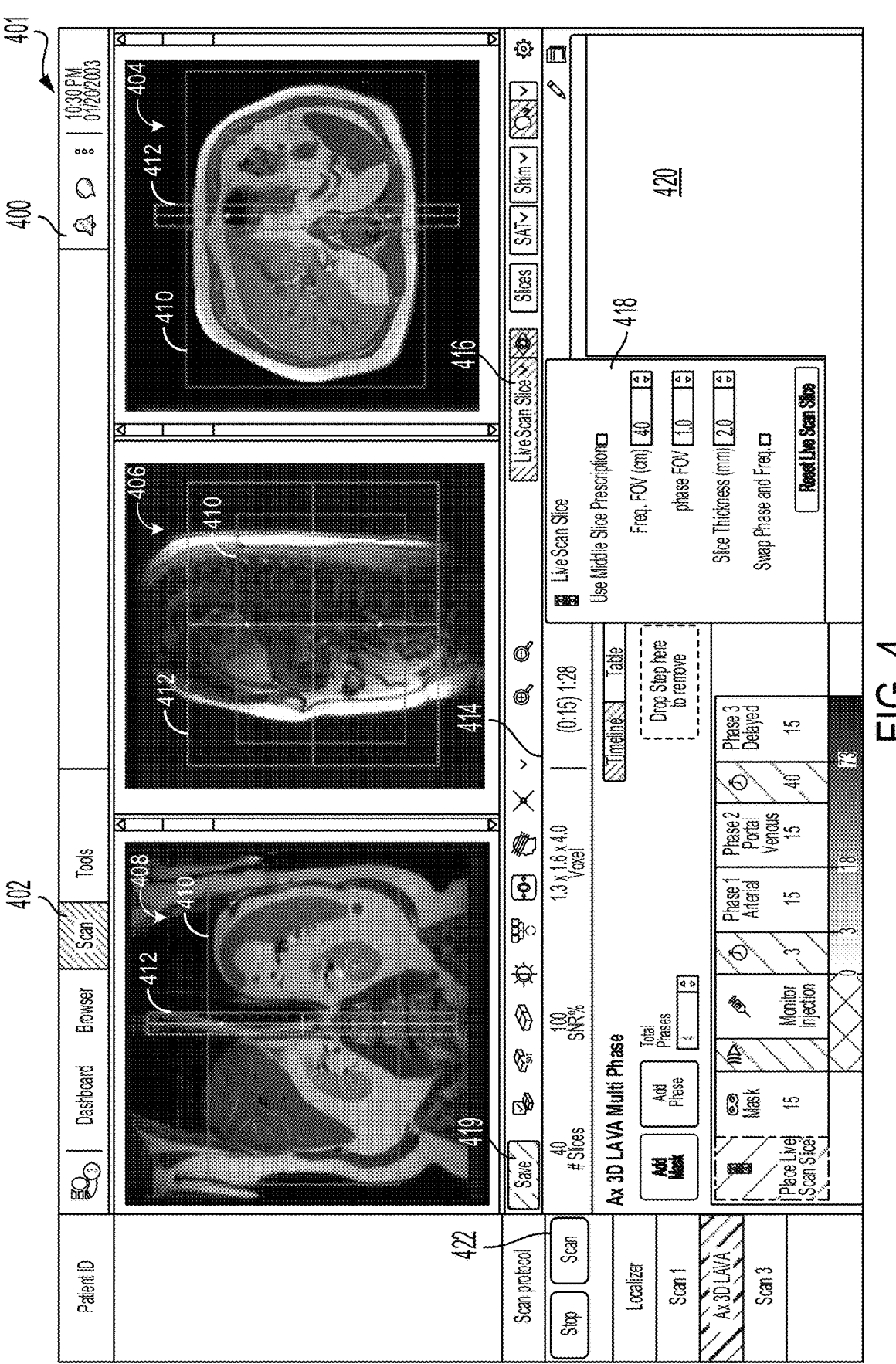
FIG. 4 illustrates an example scan interface in a first state during a first stage of a contrast scan.
Figure 5:
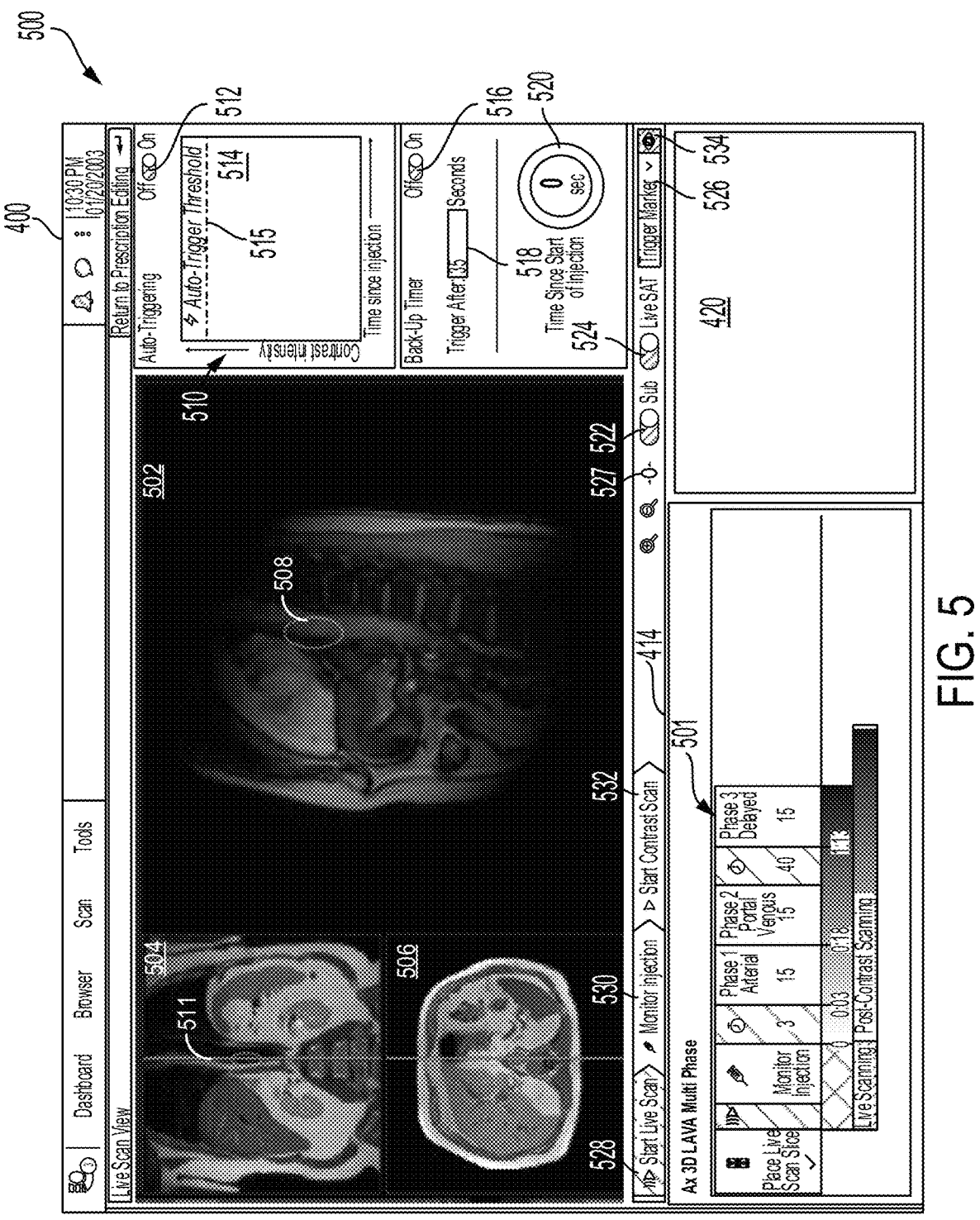
FIG. 5 illustrates the scan interface in a second state during a second stage of the contrast scan.
Figure 6:
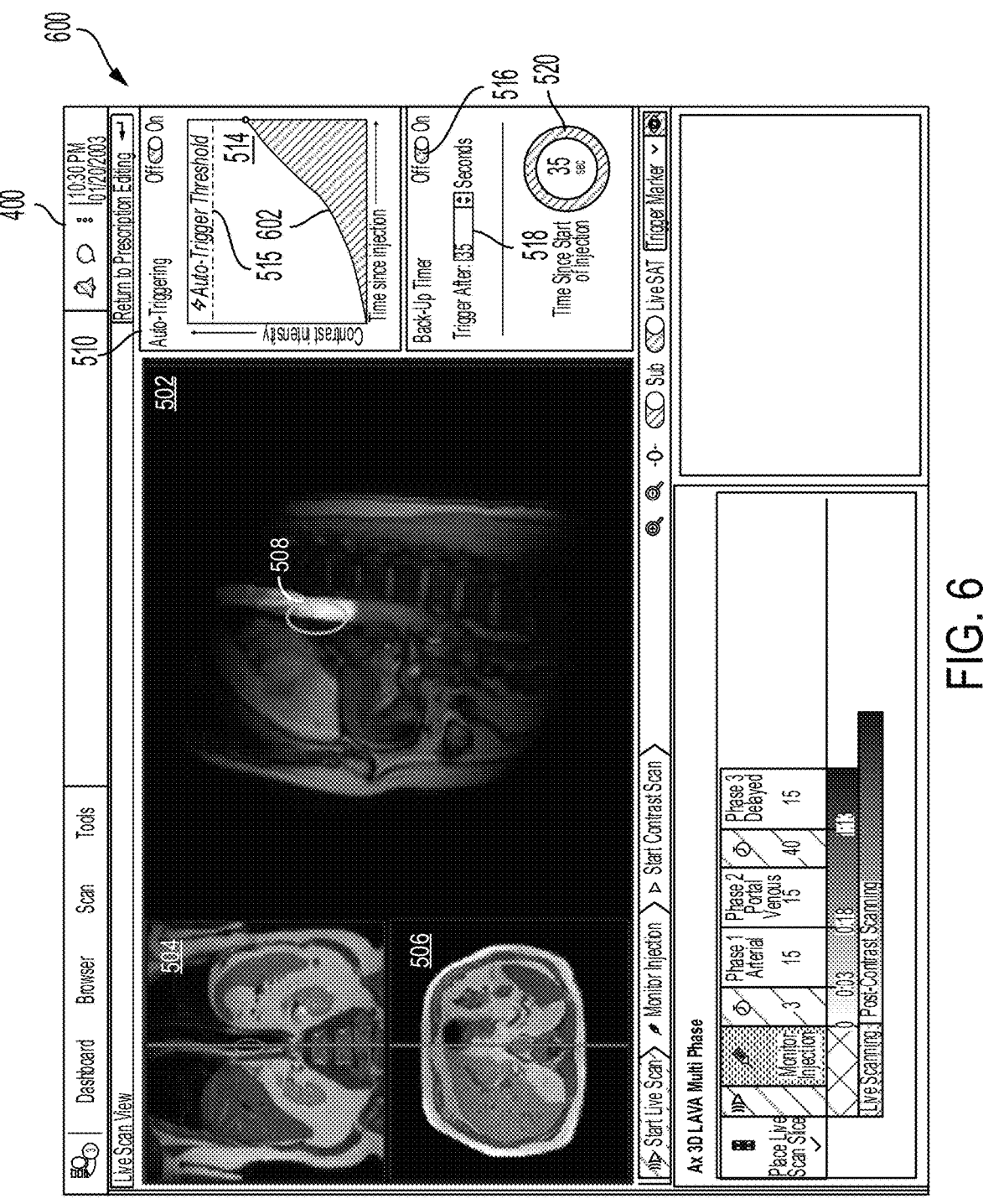
FIG. 6 illustrates the scan interface in a third state during a third stage of the contrast scan.
Figure 7:
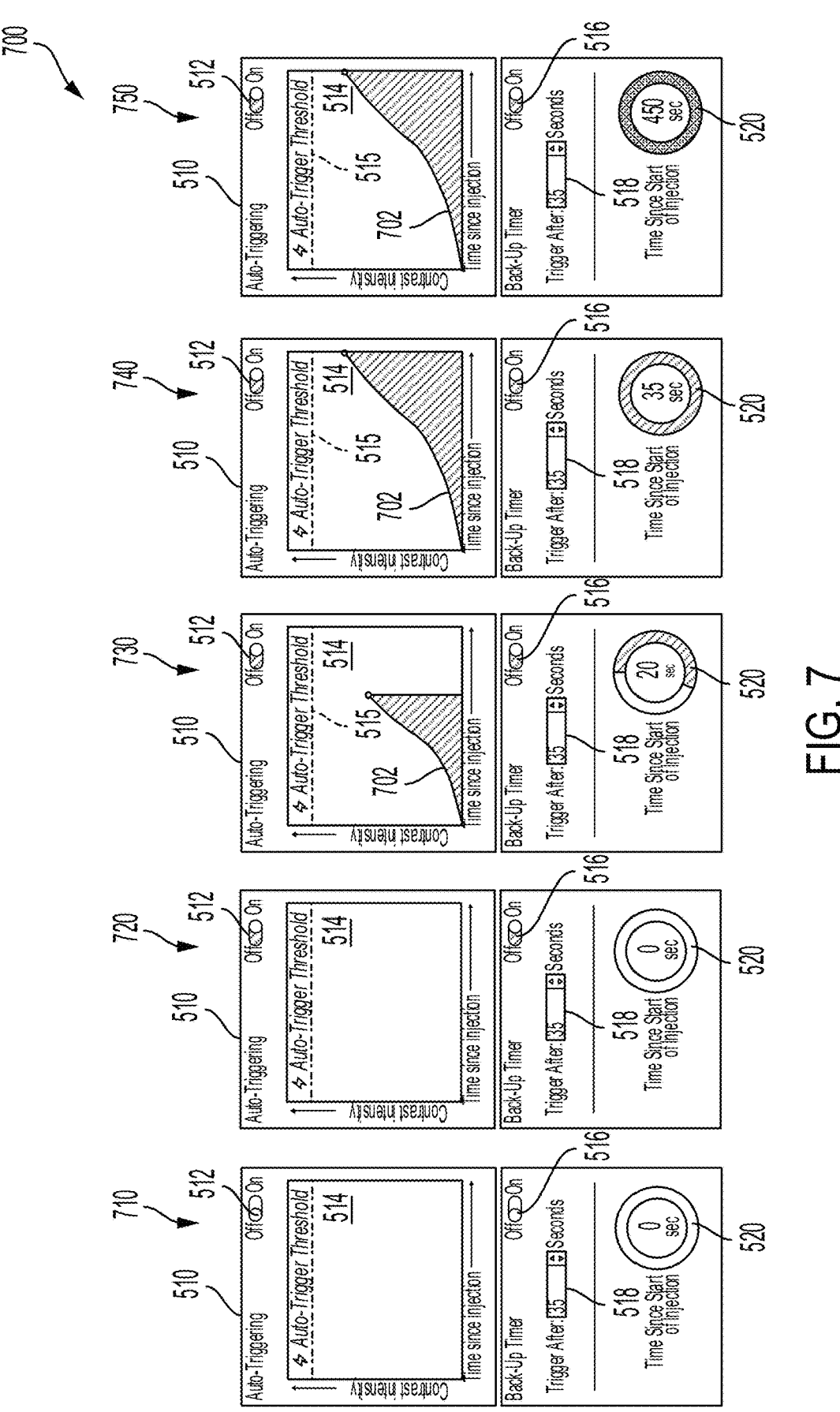
FIG. 7 illustrates a contrast plot and timer of the scan interface over time during a contrast scan.

An example MRI apparatus that may be used to obtain images of an imaging subject during a contrast-enhanced MRI scan is shown in FIG. 1. The MRI apparatus may include a scan control device, such as the scan control device of FIG. 2, configured to process data from the MRI apparatus to form images, command actions of the MRI apparatus (e.g., start the contrast scan acquisitions), and display a scan interface to enable a user to monitor a contrast level of an imaging subject during the scan, set scan prescription parameters, and the like. The scan control device may carry out actions as dictated by the user, via the scan interface, to control the MRI apparatus during the contrast scan, such as according to the timeline shown in FIG. 3. During the course of the contrast scan, the scan interface may be in various states depending on the stage of the contrast scan, as shown in FIGS. 4-6. The scan interface may include a contrast plot and a timer that may be updated as the administered contrast bolus moves to the ROI, as shown in FIG. 7. The scan control device may carry out various methods to facilitate a contrast scan, such as methods shown in FIGS. 8, 9A and 9B, and 14.

Figure 10:
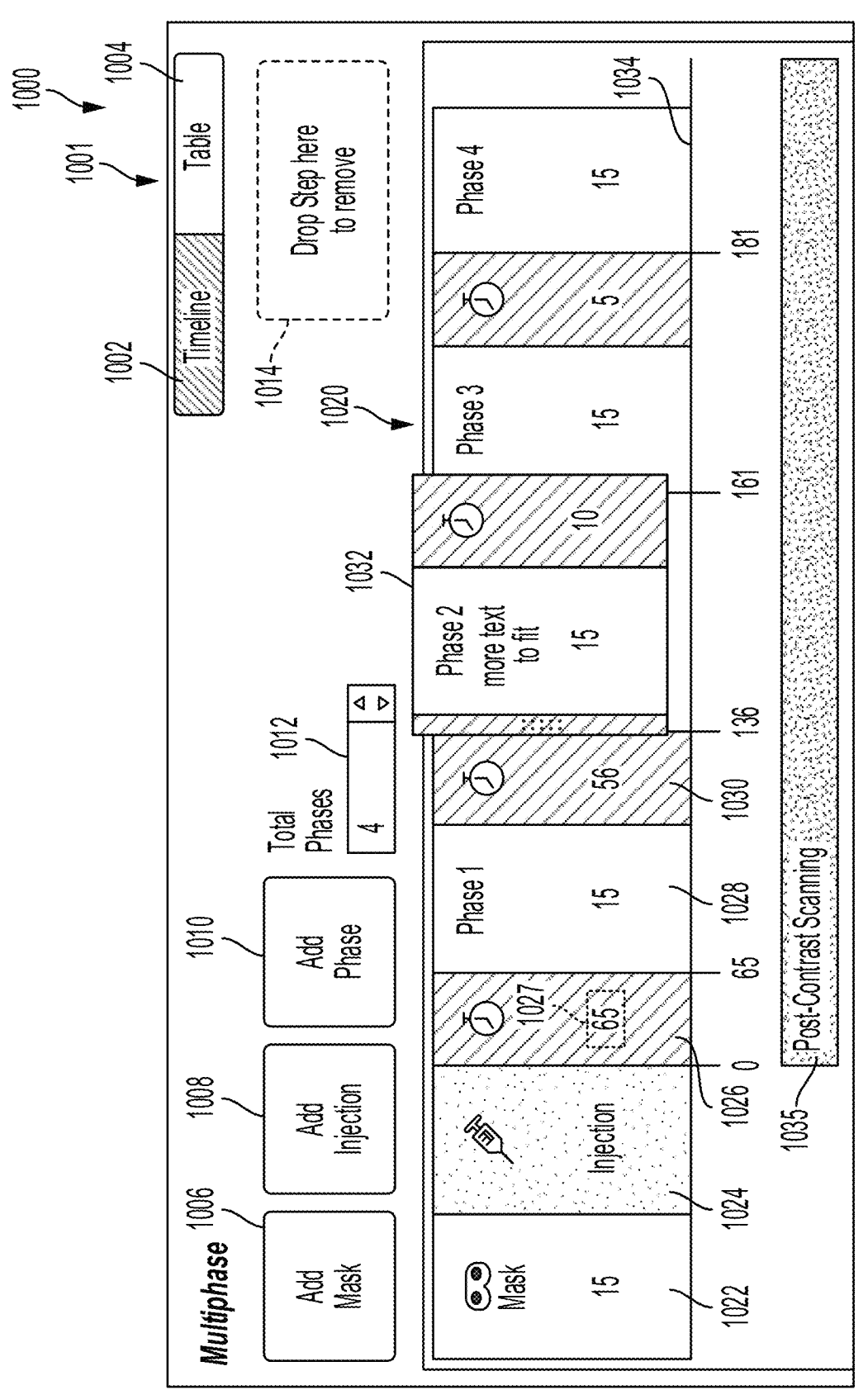
FIG. 10 shows an example of a scan prescription display panel in a first timeline view.
Figure 11:
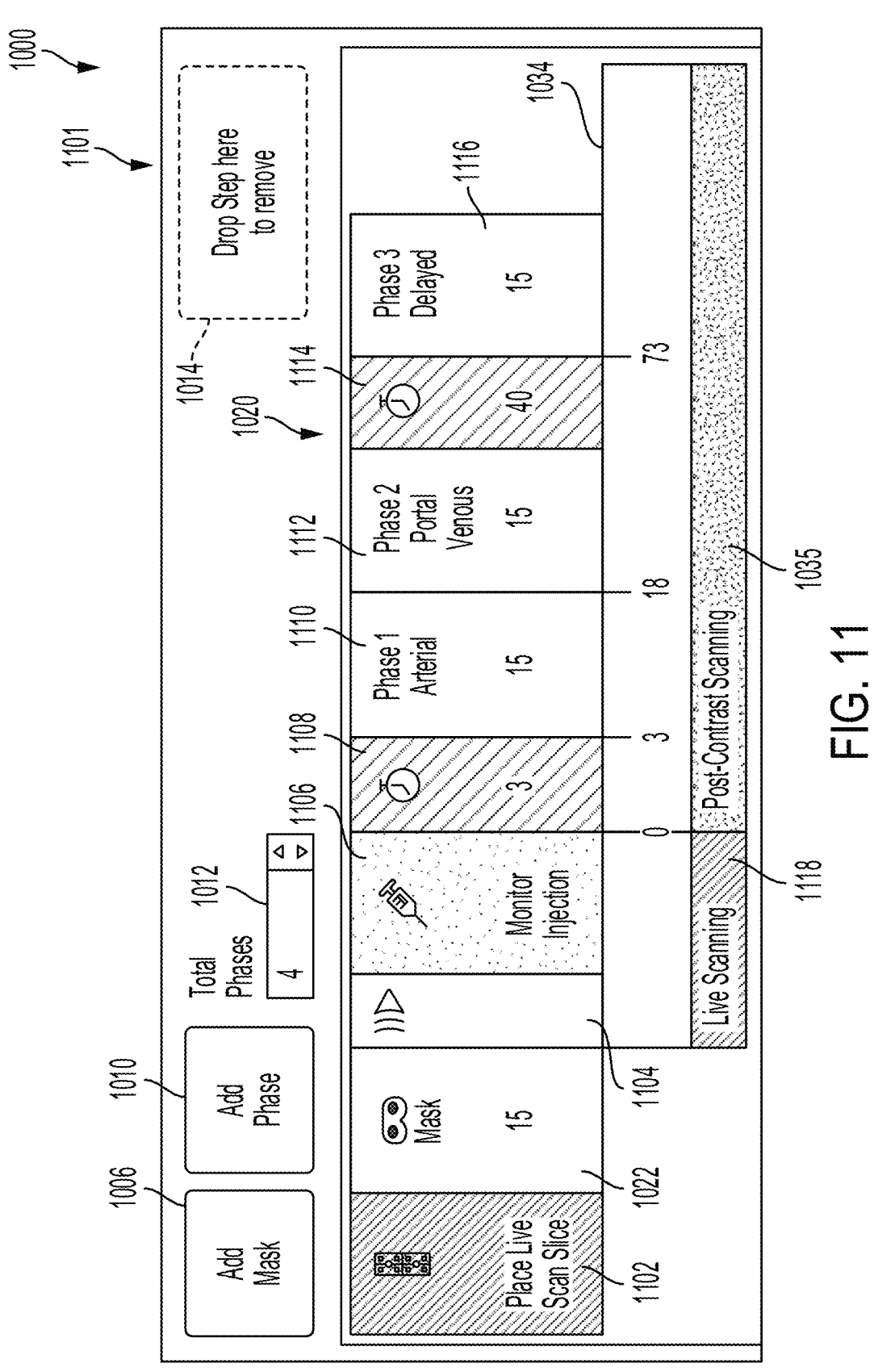
FIG. 11 shows the example of the scan prescription display panel in a second timeline view.
Figure 12:
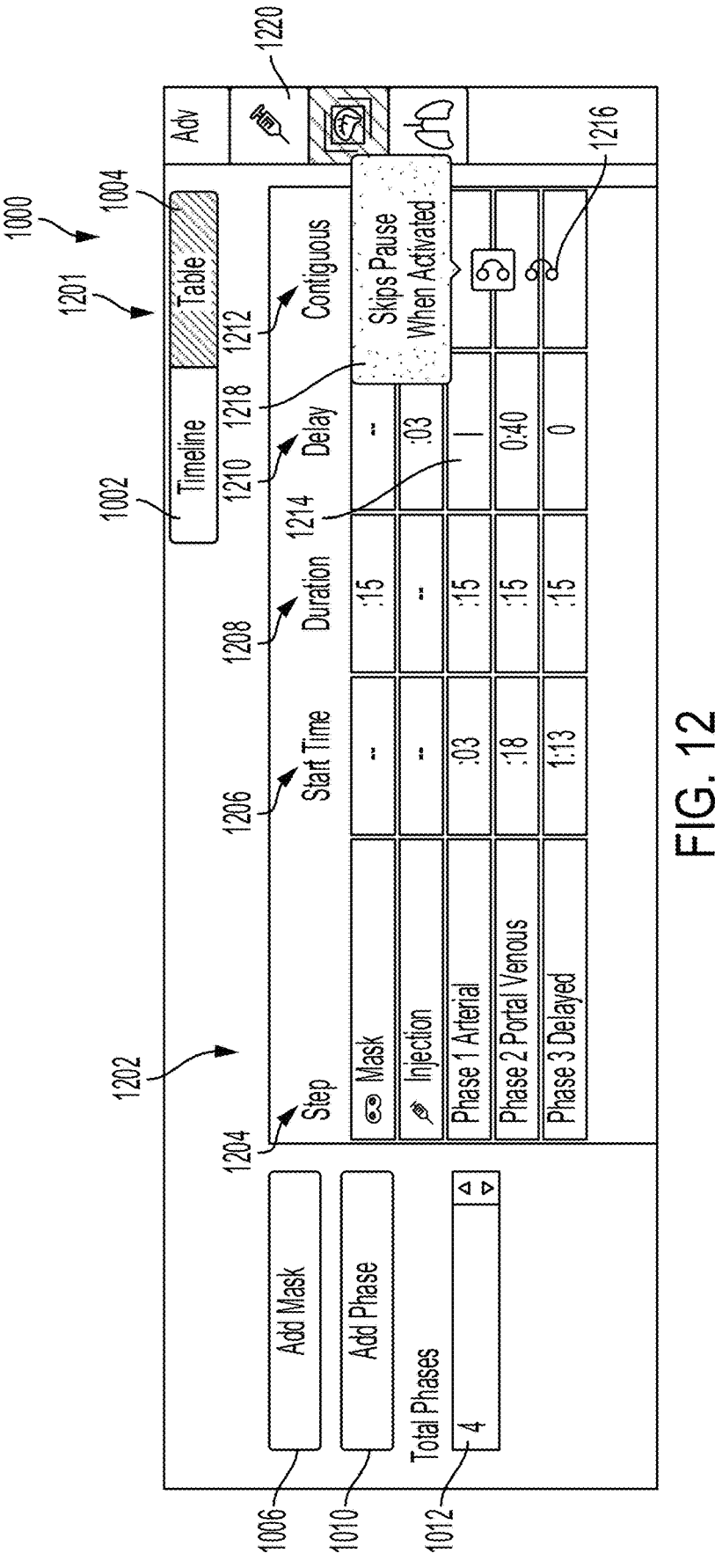
FIG. 12 shows the example of the scan prescription display panel in a table view.
Figure 13:
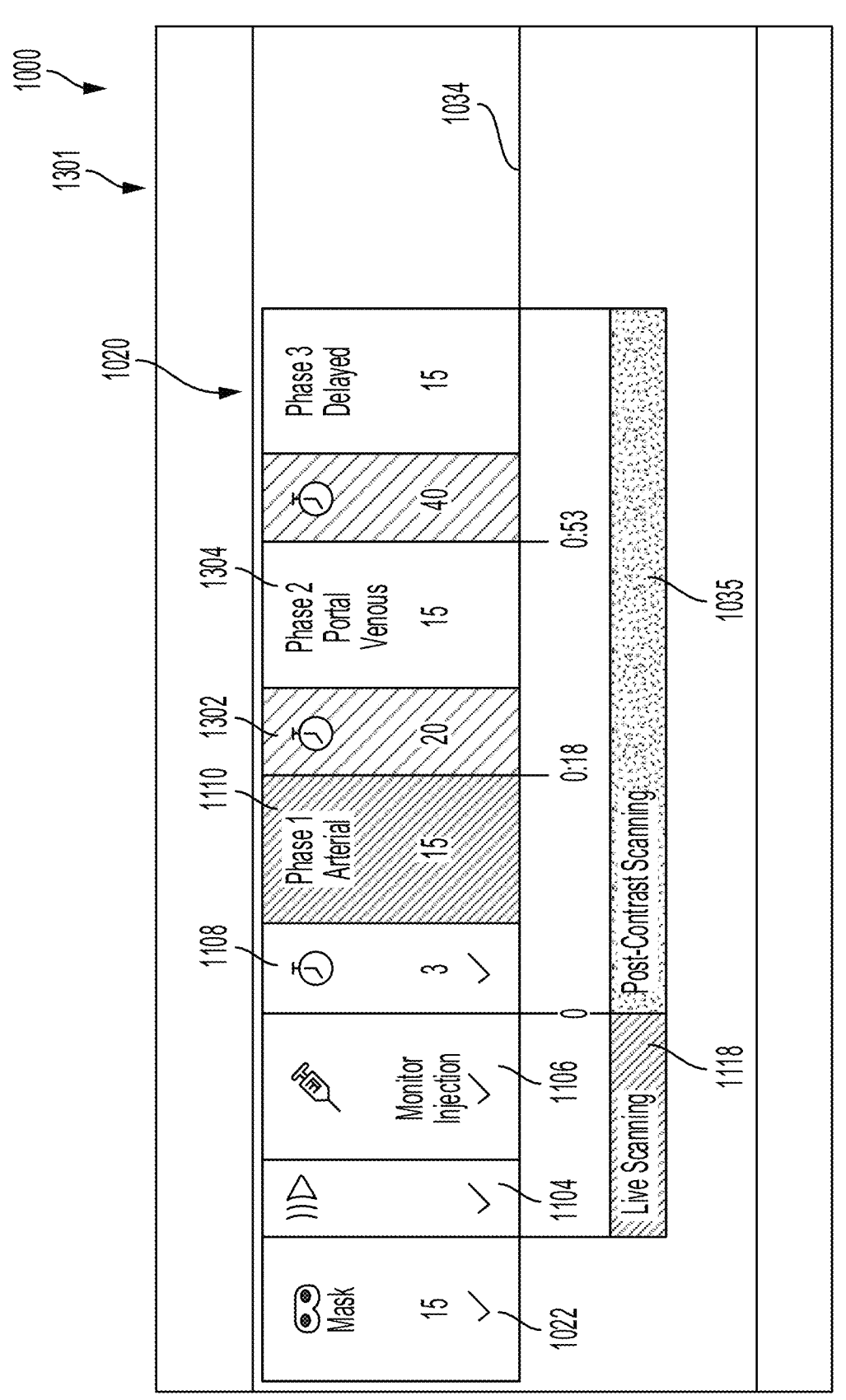
FIG. 13 shows the example of the scan prescription display panel in a scanning view.

The scan interface may further include a scan prescription display panel whereby a user may set parameters for carrying out the contrast scan. As shown in FIGS. 10 and 11, the scan prescription display panel may include a timeline view whereby the scan prescription settings (e.g., number of phases, delay times, etc.) may be updated and viewed in a timeline format. In some examples, as shown in FIG. 12, the user may toggle between the timeline view and a table view wherein the scan prescription may be viewed and updated via a table format. Once the scan prescription is set, the scan prescription timeline may be displayed on the scan interface to enable the user to visually monitor the current stage of the contrast scan, as shown in FIG. 13.

FIG. 1 illustrates an MRI apparatus 10 (e.g., an MRI system) that includes a magnetostatic field magnet unit 12, a gradient coil unit 13, an RF coil unit 14, an RF body coil unit 15 (e.g., volume coil unit), a transmit/receive (T/R) switch 20, an RF driver unit 22, a gradient coil driver unit 23, a data acquisition unit 24, a controller unit 25, a patient bed or table 26, a data processing unit 31, a scan control device 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface of the RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF body coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF body coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF body coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the scan control device 32 and processes the operation signals input to the scan control device 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the scan control device 32.

The scan control device 32 includes user input devices such as a touchscreen, keyboard and a mouse. The scan control device 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the scan control device 32. The display unit 33 also displays a two-dimensional (2D) slice image or three-dimensional (3D) image of the subject 16 generated by the data processing unit 31.

During an MRI scan using the MRI apparatus 10, a subject may be positioned within the imaging space 18 and an acquisition protocol may be carried out to obtain MR signals of the subject. The acquisition protocol may include a plurality of pulse sequences where in each pulse sequence, contrast is prepared via one or more RF pulses applied by the RF body coil unit 15 and the gradient coil unit 13 is controlled to spatially encode the resultant MR signals. The spatially-encoded MR signals are received by the RF coil unit 14 are digitized and stored in k-space. Thus, k-space data or a k-space dataset may refer to the raw MR signals prior to processing into an image. In some examples, one line of k-space may be filled with the raw MR signals per pulse sequence (also referred to as repetition time). In other examples, one line of k-space may be filled with the raw MR signals per echo, where more than one echo is generated per pulse sequence/repetition time. The k-space data may also be referred to as imaging data or MR data herein.

Figure 2:
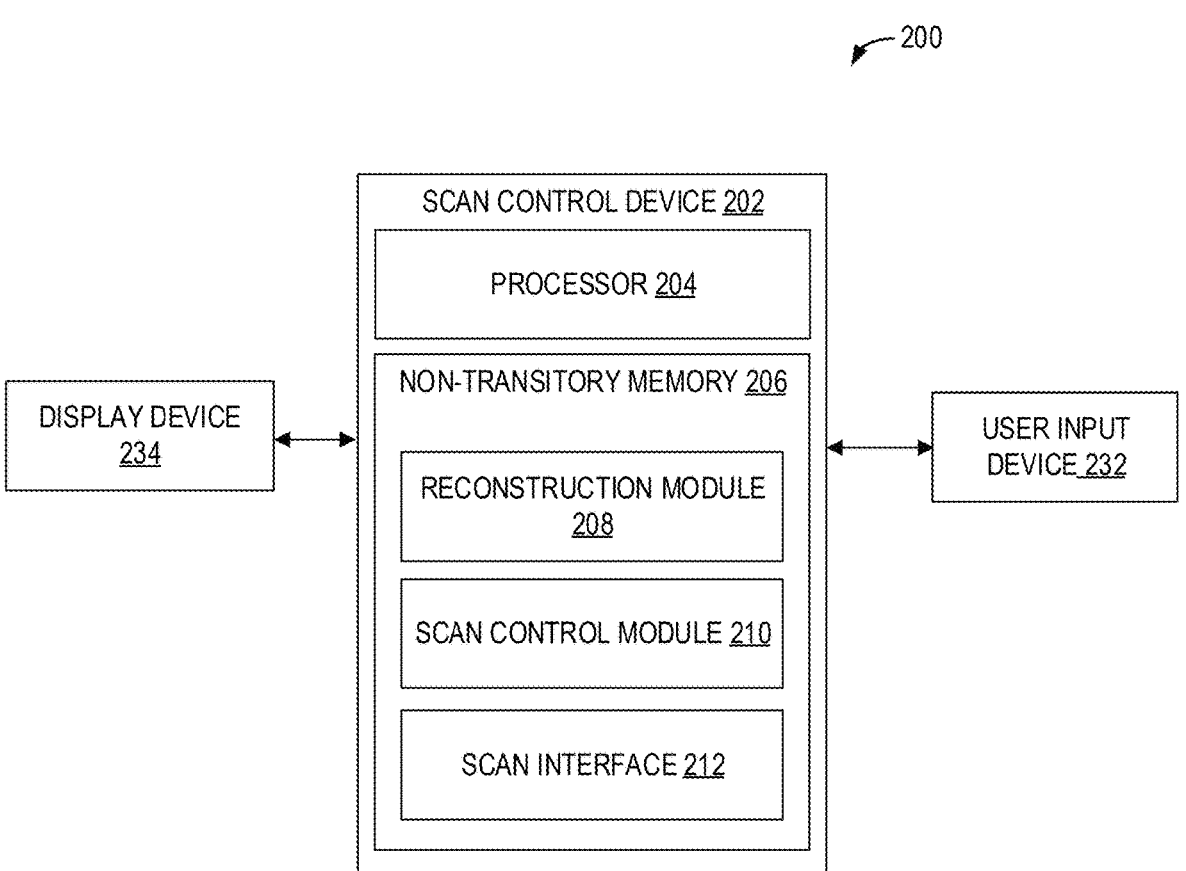
FIG. 2 schematically shows an example scan control device of the MRI apparatus of FIG. 1.

Referring to FIG. 2, scan control device 202 configured to control scan parameters of an MRI scan is shown. In some embodiments, scan control device 202 is incorporated into the MRI apparatus 10. For example, scan control device 202 may be provided in the MRI apparatus 10 as scan control device 32. In some embodiments, at least a portion of scan control device 202 is disposed at a device (e.g., edge device, server, etc.) communicably coupled to the MRI apparatus 10 via wired and/or wireless connections. In some embodiments, at least a portion of scan control device 202 is disposed at a separate device (e.g., a workstation) which can communicate with the controller unit of the MRI apparatus, for example. Scan control device 202 may be operably/communicatively coupled to a user input device 232 and a display device 234. In some examples, the user input device 232 may be the user input device of scan control device 32, explained above. Likewise, display device 234 may be the display unit 33 of MRI apparatus 10.

Scan control device 202 includes one or more processors, such as processor 204, configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a reconstruction module 208, a scan control module 210, and a scan interface 212. Reconstruction module 208 may be configured to reconstruct images from k-space data. In some examples, reconstruction module 208 may be the data processing unit 31 of FIG. 1, such that the data processing unit and scan control device are integrated into a single device. However, in other examples, reconstruction module 208 may be omitted and scan control device 202 may be in communication with the data processing unit 31 to obtain images for display.

Scan control module 210 may be configured to send commands to the MRI apparatus (e.g., to controller unit 25) in order to control aspects of a scan carried out by the MRI apparatus. Scan control module 210 may control aspects of the scan based on user input, which may be received via the scan interface 212, in some examples. For example, the scan interface 212 may include a scan prescription display panel via which a user may set parameters for the scan (e.g., the number of phases, delay time between phases). The scan interface 212 may further include various scan control buttons, such as a live scan button that, when selected by a user, is configured to trigger acquisition and display (on the scan interface 212) of live 2D images and a start contrast scan button that, when selected, is configured to trigger acquisition of post-contrast (e.g., 3D) images. Scan control module 210 may process the acquired live 2D images in order to measure contrast level in an ROI, and the scan interface 212 may display a plot of the measured contrast level over time. Additional details about the scan interface 212 and scan control module 210, including what is displayed via the scan interface 212 during a contrast scan and what actions are taken by the scan control module 210 during the contrast scan, are provided below with respect to FIG. 3.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within scan control device 202. In one example, user input device 232 may enable a user to make a selection of a scan protocol, adjust scan prescription settings, select or adjust a contrast-tracking region, and the like, as well as initiate, pause, and adjust scanning.

Display device 234 may include one or more display devices utilizing virtually any type of technology. In some embodiments, display device 234 may comprise a computer monitor, and may display MR images, including images reconstructed by reconstruction module 208. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view MRI images produced by an MRI system, and/or interact with various data stored in non-transitory memory 206.

It should be understood that scan control device 202 shown in FIG. 2 is for illustration, not for limitation. Another appropriate image processing system may include more, fewer, or different components.

Figure 3:
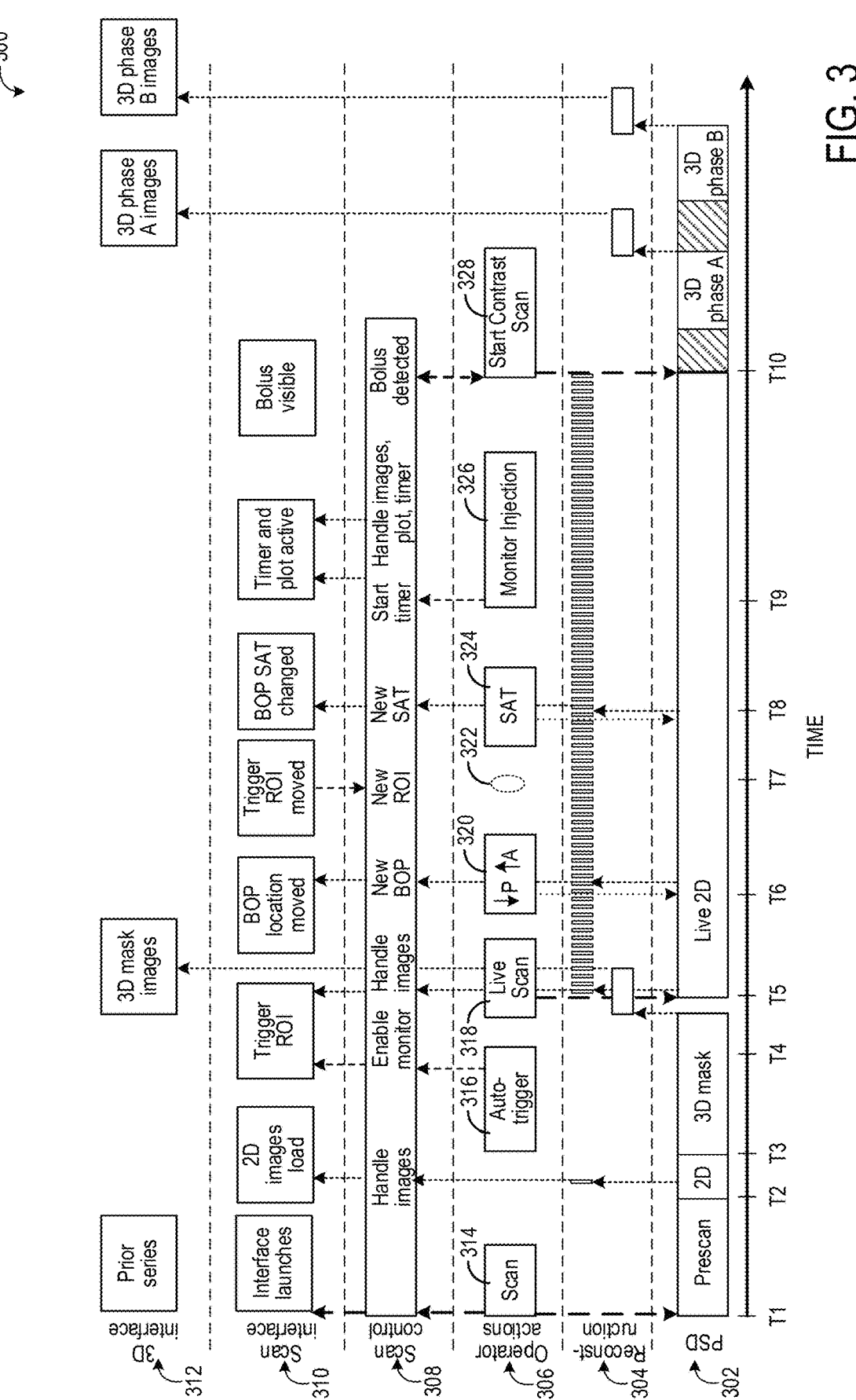
FIG. 3 shows a timeline of events carried out by the scan control device of FIG. 2 during a contrast scan, according to embodiments of the disclosure.

FIG. 3 is an example swimlane diagram 300 showing actions/events that may occur during a contrast scan of a subject using the MRI apparatus of FIG. 1, including the scan control device of FIG. 2. Diagram 300 depicts events/actions over time, with time depicted on the horizontal axis, for a plurality of aspects of the MRI apparatus that are depicted along the vertical axis, including the actions taken by the MRI apparatus (and particular the MRI scanner) in lane 302 (specifically, a pulse sequence diagram (labeled "PSD" in FIG. 3) that depicts the pulse sequence carried out by the scanner to facilitate image acquisition), the image reconstruction module in lane 304 (labeled "Reconstruction" in FIG. 3), operator interactions with the scan interface in lane 306 (labeled "Operator actions"), actions taken by the scan control module ("Scan control") in lane 308, the display status/state of the scan interface in lane 310 ("Scan interface"), and the display status/state of a 3D interface ("3D interface") configured to display acquired 3D images in lane 312. The image reconstruction module may perform both 2D image reconstruction and 3D image reconstruction, and 2D image reconstruction is depicted in lane 304 of FIG. 3 as the small rectangles while 3D image reconstruction is depicted in lane 304 as the larger rectangles positioned immediately below the 2D image reconstruction. Communication between devices/modules (e.g., between the scan control module and the controller unit of the MRI apparatus) is shown via the vertical arrows in FIG. 3. Time points of interest are depicted along the horizontal axis. It is to be appreciated that the term "MRI scanner" or "scanner" as used herein may refer to the components of the MRI apparatus that are activated to produce and receive MR signals (such as the magnetostatic field magnet unit 12, the gradient coil unit 13, the RF coil unit 14, and the RF body coil unit 15), as well as the associated control components (e.g., the RF driver unit 22, the gradient coil driver unit 23, the data acquisition unit 24, and the controller unit 25).

The contrast scan may commence at time T1 in response to operator selection of a Scan button 314 on the scan interface or a separate interface. Selection of the Scan button 314 causes the scan control module to command the scanner to initiate a prescan pulse sequence, which may include various subject-specific calibrations of the MRI apparatus. Additionally, selection of the Scan button 314 causes the scan interface to be launched. The scan interface, when initially launched, may include viewports for displaying 2D images, a scan prescription display panel, and various user interface elements to facilitate selection of a contrast observation slice/plane for observing contrast enhancement, a trigger ROI for measuring the contrast level, and so forth. The slice/plane for observing contrast enhancement may be referred to as the bolus observation plane (BOP). Because imaging has yet to commence, no images are initially displayed in the scan interface. Via the scan prescription display panel, the operator may set parameters for the scan, such as the number of 3D contrast phases, whether or not 3D mask images are to be obtained, delays or pauses in the scan, and so forth. Optionally, prior images of the subject may be displayed in the 3D interface.

After the prescan phase, the scanner may perform an initial 2D acquisition at time T2, which may result in reconstruction of a single 2D image in each of three scan planes (e.g., axial, sagittal, and coronal). The scan control module may receive the initial 2D images and load the 2D images into the viewports of the scan interface. The operator may indicate the anatomy of interest to be scanned via placement of a first box/rectangle over the displayed 2D images. The operator may also indicate the BOP (e.g., the anatomical region for observing the contrast level of the subject) via a second box/rectangle over the displayed 2D images. Once the operator selects/indicates the BOP, the image in that plane may be displayed in a main viewport (referred as the BOP viewport) and the other images (which show the orthogonal views) may be displayed in smaller reference viewports. After the initial 2D acquisition, the scanner may perform 3D mask imaging at time T3, in the background (e.g., without changing what is displayed via the scan interface), and the 3D mask images may be displayed in the 3D interface as the 3D mask images are reconstructed. The 3D mask images are images of the anatomy acquired prior to contrast administration for use in comparison and for creating subtracted images which layer the pre- and post-contrast images to show differences.

While the 3D mask imaging is occurring, the operator may interact with the scan interface to enable or disable auto-triggering and set the trigger ROI. Auto-triggering may include the automatic initiation of the post-contrast 3D acquisitions (e.g., the MR signal acquisition following administration of a contrast bolus for generation of diagnostic images), based on an automatic measurement of the contrast level in the subject following administration of the contrast bolus. The trigger ROI may be the area of the BOP that is evaluated in order to automatically measure the contrast level in the subject. For example, as shown in FIG. 3, the operator may select a user interface button (e.g., an auto-triggering button 316) at time T4 to enable auto-triggering monitoring, and a trigger ROI may be placed on the images displayed on the scan interface. The trigger ROI may be initially placed in a default location, and the operator may move the trigger ROI, resize the trigger ROI, etc. Further, it is to be appreciated that the operator may enable or disable auto-triggering at any point prior to the start of the post-contrast 3D acquisitions.

After the 3D mask imaging is complete, the scanner may pause until the operator initiates live 2D scanning. The operator may initiate live 2D scanning by selecting a live scanning button, e.g., a Start Live Scan button 318 of the scan interface, at time T5. Once the Start Live Scan button 318 is selected, the scan control module may command the scanner to commence live 2D scanning. During live 2D scanning, the scanner may perform acquisitions of MR signals (referred to as live 2D acquisitions) that are reconstructed into low resolution, 2D images. The live 2D acquisitions may be performed at a relatively high rate and the 2D images reconstructed from the MR signals may be displayed in real-time, as the images are reconstructed, in the viewports of the scan interface. In some examples, the 2D images may be displayed at a frame rate of two frames per second, although other frame rates are possible without departing from the scope of this disclosure.

While the live 2D scanning is occurring, the operator may interact with the scan interface to make various adjustments, if desired. For example, at time T6, the operator may move the BOP plane in an anterior or posterior direction, for example, via BOP movement elements 320 (e.g., a line and/or arrows that are placed over the reference images in the reference viewports). If the operator adjusts the BOP plane, the scan control module notifies the scanner to change the slice that is being acquired, and the slice of the images displayed in the BOP viewport changes accordingly. In some examples, the operator may move the trigger ROI at time T7, by dragging the trigger ROI 322 that is displayed on the live 2D images and/or by selecting a trigger marker button and then entering keystrokes (e.g., side arrows, up/down arrows) to move the trigger ROI. In still further examples, the operator may enable or disable saturation (SAT) at time T8 for the BOP image by selecting a SAT button 324 on the scan interface. Other adjustments are possible as well, such as enabling or disabling image subtraction for the BOP image. Because the measurement of the contrast level includes a measurement of the baseline, non-contrast pixel brightness in the BOP image at the trigger ROI (e.g., for comparison as the brightness increases with contrast uptake), adjusting the BOP location, saturation, trigger ROI location/size, or image subtraction entails acquisition of a new baseline, non-contrast BOP image (e.g., new 3D mask images).

Once the operator has set the scan prescription and is satisfied with the BOP location, auto-triggering settings, and is otherwise ready for the 3D contrast acquisitions to begin, the contrast bolus is injected to the subject. Upon initiation of the injection of the contrast agent, the operator selects a monitoring button, such as the Monitor Injection button 326, of the scan interface, such as at time T9. The selection of the Monitor Injection button 326 triggers the scan control module to start a back-up timer. Additionally, the selection of the Monitor Injection button 326 also triggers the scan control module to start measuring the contrast level in the trigger ROI and generate a plot of the measured contrast level over time. Both the timer and the plot are displayed in the scan interface and are updated at a relatively high rate, e.g., at the frame rate of the live 2D imaging. As such, the contrast plot may be a live plot that includes a real-time curve of contrast intensity over time. Live 2D scanning is ongoing and the live 2D images are displayed in the scan interface. As the contrast bolus arrives at the trigger ROI, the brightness of the BOP image, at least at the trigger ROI, increases and the contrast bolus becomes visible on the scan interface, which is visually indicated via both the live 2D images and the contrast plot.

The post-contrast scan commences in response to any of three possible triggers. If auto-triggering is enabled, the post-contrast scan commences once the measured contrast level reaches a threshold level. Alternatively, for example if auto-triggering is not enabled, the post-contrast scan may commence once the operator selects a contrast scanning button, such as the Start Contrast Scan button 328, of the scan interface. In either example, the post-contrast scan may commence once the back-up timer reaches a threshold duration, if the threshold duration is reached before the measured contrast level reaches the threshold or before the operator selects the Start Contrast Scan button 328. The post-contrast scan may include one or more phases of 3D image acquisition optionally separated by delays. For example, FIG. 3 shows the post-contrast scan commencing at time T10, where the post-contrast scan includes two image-acquisition phases (3D phase A and 3D phase B), with the first phase commencing after a delay and the second phase commencing after the first phase and an intervening delay. At least in some examples, the pulse sequences carried out for the post-contrast scan may be different than the pulse sequences carried out to acquire the live 2D images. Once the 3D images have been reconstructed, the 3D post-contrast images are displayed via the 3D interface.

FIG. 4 shows an example of a scan interface 400 in a prescription view 401. The scan interface 400 may be the scan interface 212 of FIG. 2 and thus may include the features discussed above with respect to FIG. 3. The scan interface 400 may be displayed in the prescription view 401 before live 2D scanning has commenced. In FIG. 4, the scan interface 400 in the prescription view 401 is shown as being displayed after the initial 2D image acquisition has occurred and before live 2D scanning has commenced (e.g., between times T2 and T5 of FIG. 3). The scan interface 400 in the prescription view 401 may be displayed in response to user selection of a scan tab 402.

The 2D images from the initial 2D acquisition may be displayed in three viewports of the prescription view 401. A first image 404 is displayed in a first viewport, a second image 406 is displayed in a second viewport, and a third image 408 is displayed in a third viewport. In the example shown, the first image 404 is an axial view, the second image 406 is a sagittal view, and the third image 408 is a coronal view, each reconstructed from the k-space data acquired during the initial 2D acquisition. A user (e.g., the operator of the MRI apparatus (e.g., a technician)) may prescribe the field of view (e.g., anatomy of interest) to be scanned in the contrast scan by placing/moving/resizing a first box 410 onto each of the three images. The contrast scan being prescribed in the example shown herein is a liver acceleration volume acquisition (LAVA) scan, and thus the first box 410 is placed to scan the liver. Further, the operator may place/move/resize a second box 412 onto an anatomical feature (e.g., a vessel) of each of the three images to designate a slice for contrast tracking (also referred to as the BOP or contrast observation slice). Based on the placement of the second box 412, the BOP slice/contrast observation slice is determined. The scan interface 400 in the prescription view 401 further includes a live scan slice menu 416, which when selected causes a live scan slice display panel 418 to be displayed. Via the live scan slice display panel 418, the operator may make adjustments to the live scan slice (e.g., the BOP slice), such as the frequency and phase FOVs and slice thickness.

The scan interface 400 in the prescription view 401 further includes a scan prescription display panel 414. The scan prescription display panel 414 may include various user interface elements that may be selected or adjusted in order to set or edit the number of 3D scanning phases and associated delays of the scan prescription for carrying out the contrast scan. In the example shown in FIG. 4, the timeline view of the scan prescription display panel is shown, with the phases and delays depicted as a function of time. Further details on the scan prescription display panel 414 are provided below with respect to FIGS. 10-14. Once the operator is finished editing the scan prescription, the operator may select a Save button 419, which may save the changes made to the scan prescription.

The scan interface 400 in the prescription view 401 may also include an instructions panel 420 wherein instructions, tips, etc., for interacting with the scan interface 400 may be displayed. For example, in the prescription view 401, the instructions panel 420 may instruct the operator on the purpose of the first box 410, the second box 412, the live scan slice menu 416, and the scan prescription display panel 414.

The scan interface 400 in the prescription view 401 includes additional panels, such as patient information panels (e.g., including patient identifying information such as name and/or patient ID) and a scan protocol panel. The scan protocol panel may list the scans that are to be carried out on the patient, such as a localizer scan, the contrast scan, and/or any other scans (e.g., a screening scan, such as a single-shot fast spin echo), and the scans listed may change in visual appearance to indicate which scans have already been carried out, which is the current scan, and which scans are left to carry out. The scan protocol panel may further include a scan button 422, which may be an example of the scan button 314. Selection of the scan button 422 may launch a live scanning view of the scan interface, described in more detail below. It is to be appreciated that the scan button 422 may be positioned elsewhere on the scan interface without departing from the scope of this disclosure.

Thus, the prescription view 401 of the scan interface 400 allows for the operator to prescribe or place, prior to being shown the live view of the patient's anatomy, a rectangle to indicate to the system which anatomical region is of interest. Via the prescription view of the scan interface, the operator may also construct a timeline-based series of phases, or steps, that they want the exam to use, referred to as the scan prescription.

FIG. 5 shows a live scanning view 500 of the scan interface 400. The scan interface 400 may be displayed in the live scanning view 500 after the second box 412 has been placed and thus the BOP has been designated, after the operator has saved (e.g., by selecting the Save button 419) any changes made to the scan prescription via the scan prescription display panel 414, and after the operator has selected the scan button 422. The live scanning view 500 may initially show the previously acquired 2D images, until the operator initiates live scanning via a Start Live Scan button 528. For example, upon selection of the Save button 419 in the prescription view 401, the scan prescription display panel 414 may be updated to show a scanning view 501 of the scan prescription and some of the interface elements (e.g., the Save button 419) may be replaced with new interface elements, including the Start Live Scan button 528. Once selected, the Start Live Scan button 528 may change in visual appearance (e.g., change color) to indicate that the scan is currently in the live 2D scanning phase. The scanning view 501 may include a timeline that visually indicates any earlier steps of the scan prescription that are complete (e.g., via a check mark) as well as visually indicate the current step of the scan prescription.

Thus, the live scanning view 500 may be a live, real-time scanning view wherein the images displayed are updated in real-time as new images are reconstructed from continuously-acquired k-space data. The images are displayed in a main, BOP viewport 502, a first reference viewport 504, and a second reference viewport 506. The BOP viewport 502 may include images of the BOP (e.g., the contrast observation slice), as explained previously, and the reference viewports may include images in the planes orthogonal to the BOP. For example, the BOP viewport 502 shows a live image in the sagittal plane, the first reference viewport 504 shows an image in the coronal plane, and the second reference viewport 506 shows an image in the axial plane. The BOP viewport 502 may be larger than the reference viewports to emphasize the BOP/contrast observation slice.

In the live scanning view 500, the scan interface 400 further includes a contrast tracking display panel 510 that includes an auto-triggering button 512. In the example shown in FIG. 5, the operator has toggled the auto-triggering button 512 to the on position, thereby enabling auto-triggering. As a result, a trigger ROI 508 has been placed on the image in the BOP viewport 502, as well as on the images in the reference viewports. The operator may move the trigger ROI 508 by dragging the trigger ROI 508, which causes the corresponding trigger ROI on the images in the reference viewports to move as well. The reference viewports further include elements 511 (e.g., arrows) via which the BOP/contrast observation slice may be adjusted (e.g., if the operator clicks on the arrow pointing right, the BOP/contrast observation slice may be adjusted to be one slice to the right of the current slice).

The contrast tracking display panel 510 includes a contrast plot 514 that is configured to display, after live scanning has commenced and after injection of the contrast bolus, measured contrast level (e.g., intensity) as a function of time since contrast injection. The contrast plot 514 includes an auto-trigger threshold 515 that may be adjusted by the operator (e.g., via dragging the auto-trigger threshold 515 up or down). As further described herein, when the measured contrast level equals or exceeds the auto-trigger threshold 515 and auto-triggering is enabled, a post-contrast scan including one or more post-contrast acquisitions may be initiated.

The contrast tracking display panel 510 further includes interface elements for enabling and setting a back-up timer. The back-up timer may be enabled via a back-up timer button 516 and the duration of the back-up timer may be adjusted/set by the operator via a timer duration menu 518.

The timer duration menu 518 may include a box for text entry, as shown, or the timer duration menu 518 may include toggle buttons or a drop-down menu whereby the operator may select a duration from among a plurality of preset durations. When the back-up timer is enabled, the back-up timer may begin counting responsive to receiving an indication (e.g., via selection of a Monitor Injection button 530) that a contrast bolus has been injected to the imaging subject. Thus, the contrast tracking display panel 510 further includes a timer 520 that may visually indicate the time since the start of the injection.

The scan interface 400 in the live scanning view 500 includes a plurality of interface elements that may be selected/actuated in order to adjust scan settings and/or trigger various actions. For example, the live scanning view 500 includes a subtraction button 522 that the operator may toggle on or off to enable or disable image subtraction, respectively. Likewise, the live scanning view 500 includes a SAT button 524 that the operator may toggle on or off to enable or disable saturation, respectively. The live scanning view 500 additionally includes a Trigger Marker menu 526. When selected, the Trigger Marker menu 526 causes an additional menu/display panel to be displayed, via which the operator may make adjustments to the trigger ROI 508. For example, the Trigger Marker menu 526 may include inputs for adjusting the length and width of the trigger ROI numerically. The operator may also adjust those values of the trigger ROI (e.g., length and width) directly in the BOP viewport 502 by dragging anchor points on the trigger ROI 508. The anchor points may only be visible when the trigger ROI 508 is selected. Additionally, the scan interface may include a trigger icon 534 that, when selected, causes the trigger ROI 508 to be displayed and, when deselected, causes the trigger ROI 508 to be removed from the BOP viewport. Further, in some examples, the live scanning view 500 may include a reset to default button 527 that may be selected in order to revert certain settings, such as zoom level, window width/length, etc.

Further, the live scanning view 500 includes the Start Live Scan button 528, the Monitor Injection button 530, and a Start Contrast Scan button 532. Once the injection of the contrast bolus has begun, the operator may select the Monitor Injection button 530 to indicate to the scan control module to begin measuring the contrast level in the trigger ROI 508 (which would be displayed in the contrast plot 514) and start the back-up timer (which would be shown via the timer 520). If the auto-triggering is not enabled, the operator may select the Start Contrast Scan button 532 to signal to the scan control module to commence the post-contrast 3D scan (e.g., start the 3D acquisitions following any specified delay). In some examples, even if the operator does not enable auto-triggering, the contrast level may still be tracked and displayed via the contrast tracking display panel 510, which may allow the operator to make an informed decision about when to initiate the post-contrast scan. In other examples, if the operator does not enable auto-triggering, the contrast level may not be tracked, which may increase the efficiency of the scan control device by reducing the processing demands associated with tracking the contrast level. In an example, a method may include a first scan with auto-triggering, and then a second scan without auto-triggering, via the same imaging system and same user interface and protocols as described herein.

The scan interface 400 in the live scanning view 500 may also include the instructions panel 420 wherein instructions, tips, etc., for interacting with the scan interface 400 may be displayed. For example, in the live scanning view 500, the instructions panel 420 may instruct the operator on the purpose of the trigger marker, the subtraction and SAT buttons, and the Monitor Injection button.

Thus, the scan interface 400 in the live scanning view 500 provides a real-time view that may be displayed after the operator has prescribed the scan and has pressed the "start scan" button. This view includes: a constantly updating live view of the patient's anatomy; orthogonal reference viewports (two smaller viewports); a graph (upper right) showing how much contrast the scanner is registering while "watching" the region of interest; a timer (middle right) that acts as a back-up for both the operator and the system missing the identification of the bolus arrival; and a timeline that shows the operator exactly where the scanner is in the scan process. As mentioned above, the large viewport in the center is a real-time, updating view of the patient's anatomy. The two smaller viewports are orthogonal views of the same region. The line and arrows in the small reference viewports allow the operator to shift the view of the large, live view by discrete amounts.

FIG. 6 shows a bolus view 600 of the scan interface 400. The bolus view 600 may be displayed during tracking/ monitoring the contrast bolus, such as after the operator has selected the Monitor Injection button 530. The bolus view 600 may be similar to the live scanning view 500 in that live 2D images of the BOP/live scanning slice may be displayed in the BOP viewport 502, along with the trigger ROI 508 if indicated. As appreciated in FIG. 6, as the contrast agent is injected to and uptaken by the patient/imaging subject, the contrast agent becomes visible, particularly in the region of the trigger ROI. The contrast tracking display panel 510 may be updated in the bolus view 600 so that a live curve 602 depicting contrast intensity as a function of time is shown (wherein the contrast intensity is measured in the trigger ROI of the live 2D images of the BOP). Further, the back-up timer starts to increment and the timer 520 is adjusted to indicate the total time since the contrast was injected (herein, 35 seconds).

FIG. 7 shows a series of views 700 of the contrast tracking display panel 510 over the course of monitoring of a contrast bolus. The series of views 700 includes a first view 710 that may be displayed prior to auto-triggering being enabled and prior to the back-up timer being enabled. Thus, in the first view 710, the auto-triggering button 512 is in the off position and the back-up timer button 516 is in the off position. In a second view 720, the operator has toggled both the auto-triggering button 512 and the back-up timer button to respective on positions. The second view 720 may be displayed before the injection of the contrast bolus has commenced.

The series of views 700 further includes a third view 730, a fourth view 740, and a fifth view 750 that may each be displayed after the injection of the contrast bolus and after the operator has selected the Monitor Injection button. Thus, the third view 730 shows a live curve 702 depicting measured contrast intensity as a function of time in the contrast plot 514. In the third view 730, the timer 520 visually indicates the time since the injection commenced. For example, the timer 520 includes a numeric indication of the number of seconds (e.g., 20) since the injection commenced as well as a change to the color of a circle that progresses in a clockwise direction as time progresses. The rate of the color change is based on the timer duration as set via the timer duration menu 518. In the illustrated example, the operator has set the timer duration as 35 seconds, and thus the color of the circle in the third view 730 has changed from a first color (e.g., gray) to a second color (e.g., blue) for 57% of the circumference of the circle (as 20 seconds is approximately 57% of the timer duration).

In the fourth view 740, the live curve 702 has progressed toward the auto-trigger threshold 515 but the contrast intensity of the live curve 702 has not reached the auto-trigger threshold 515. However, the back-up timer has reached the timer duration, as shown by the timer 520 (e.g., the timer 520 shows that 35 seconds have elapsed since the start of injection, with the entirety of the circle being of the second color). Because the contrast level has not reached the threshold for auto-triggering the start of the post-contrast scan by the time the back-up timer duration has elapsed, the post-contrast scan may be initiated automatically by the scan control module. Alternatively, if the backup timer is disabled (e.g., set to "off"), the timer 520 may change in visual appearance (e.g., turn a third color, such as red) once the back-up timer reaches the set duration to signal to the operator to manually initiate the post-contrast scan by selecting the Start Contrast Scan button (e.g., which may be displayed in the scan protocol panel of the scan interface, e.g., the stop button shown in FIG. 4). The timer 520 may also change to red if the operator has selected the Pause Live Scan button and the live scan is in a paused state when the timer reaches the set/threshold duration.

The fifth view 750 may be displayed after the post-contrast scan has been initiated (e.g., due to the operator initiating the post-contrast scan or due to the back-up timer being enabled and reaching the set duration) and thus no further tracking of the contrast bolus has been performed. As a result, the contrast plot 514 depicts the live curve 702 at the same state as in the fourth view 740. The back-up timer has continued to run, with the timer 520 showing the time since the injection began (e.g., 450 seconds).

Thus, while the system is "watching" for contrast, the operator is shown a graph (e.g., the live curve 702) indicating how much contrast the system is observing in real time and how close to the designated threshold the contrast level has reached. Once the contrast level reaches the threshold, the 3D post-contrast acquisitions may be triggered. The operator may also set a back-up timer that starts automatically when the operator indicates that contrast has been delivered to the subject. This timer both allows the operator to know the time since injection and visualizes how close to the maximum wait time the system is before triggering the acquisition.

Thus, a computing device (e.g., scan control device 202) may include a display screen (e.g., display device 234), and the computing device may be configured to display on the screen a scan interface (e.g., scan interface 400) in a prescription view (e.g., prescription view 401). The computing device may further be configured to receive user input via the scan interface in the prescription view to enable prescription (e.g., selection) of a contrast observation slice for tracking arrival of a contrast bolus during a contrast scan, for example via the second box 412. The computing device may additionally be configured to display on the screen user interface element (e.g., the start live scan button 528 and/or the scan button 422) that can be reached directly from the scan interface in the prescription view, wherein the user interface element is selectable to launch a live scanning view (e.g., live scanning view 500) of the scan interface that enables live 2D images of the contrast observation slice to seen within the scan interface. In some examples, the user interface element may be selectable to enable live 2D scanning of the contrast observation slice, or a separate user interface element may be selected (e.g., on the live scanning view) to enable the live 2D scanning. In some examples, the live scanning view may further include a contrast tracking display panel (e.g., contrast tracking display panel 510) that displays an auto-triggering button (e.g., auto-triggering button 512) that is selectable to enable auto-triggering of post-contrast image acquisition and enable a contrast intensity plot (e.g., live curve 702 within contrast tracking display panel 510) determined from the live 2D images to be seen within the contrast tracking display panel.

In some examples, the computing device is configured to command initiation of the live 2D scanning in response to selection of the live scanning button, wherein the live 2D scanning comprises acquisition of first imaging data with a medical imaging apparatus (e.g., MRI apparatus 10) and reconstruction of the first imaging data into the live 2D images. In some examples, the computing device may be further configured to display on the screen, via the live scanning view of the scan interface, an injection button (e.g., monitor injection button 530) that is selectable to trigger measurement of contrast intensity in a trigger region of interest (ROI), such as trigger ROI 508, of the live 2D images and generation of the contrast intensity plot. In some examples, the computing device is configured to, responsive to selection of the auto-triggering button and selection of the injection button of the live scanning view, generate the contrast intensity plot by measuring the contrast intensity in the trigger ROI of each of the live 2D images acquired after the selection of the injection button and display the contrast intensity plot within the contrast tracking display panel. In some examples, the computing device is configured to command initiation of the post-contrast image acquisition in response to a contrast intensity level of the contrast intensity plot reaching a threshold intensity (e.g., threshold 515) and without further user input, wherein the post-contrast image acquisition comprises acquisition of second imaging data with the medical imaging apparatus and reconstruction of the second imaging data into one or more post-contrast images (e.g., post-contrast 3D images).

In some examples, the contrast tracking display panel further displays a back-up timer button (e.g., back-up timer button 516) that is selectable to enable commencement of a back-up timer responsive to selection of the injection button and enable a visualization of the back-up timer (e.g., timer 520) to be seen within the contrast tracking display panel, wherein the computing device is configured to command initiation of the post-contrast image acquisition in response to the back-up timer reaching a threshold duration (e.g., and without further user input).

In some examples, the live scanning view of the scan interface displays an image subtraction button (e.g., subtraction button 522) that is selectable to enable an image subtraction operation to be performed on the live 2D images. In some examples, the live scanning view of the scan interface displays a saturation button (e.g., SAT button 524) that is selectable to enable a saturation operation to be performed on the live 2D images. In some examples, the live scanning view of the scan interface displays a contrast scan button (e.g., start contrast scan button 532) that is selectable to trigger the post-contrast image acquisition. In some examples, the scan interface in the prescription view includes a scan prescription display panel (e.g., scan prescription display panel 414) that displays a scan prescription for at least the post-contrast image acquisition in a timeline format (e.g., in the scanning view 501).

Figure 8:
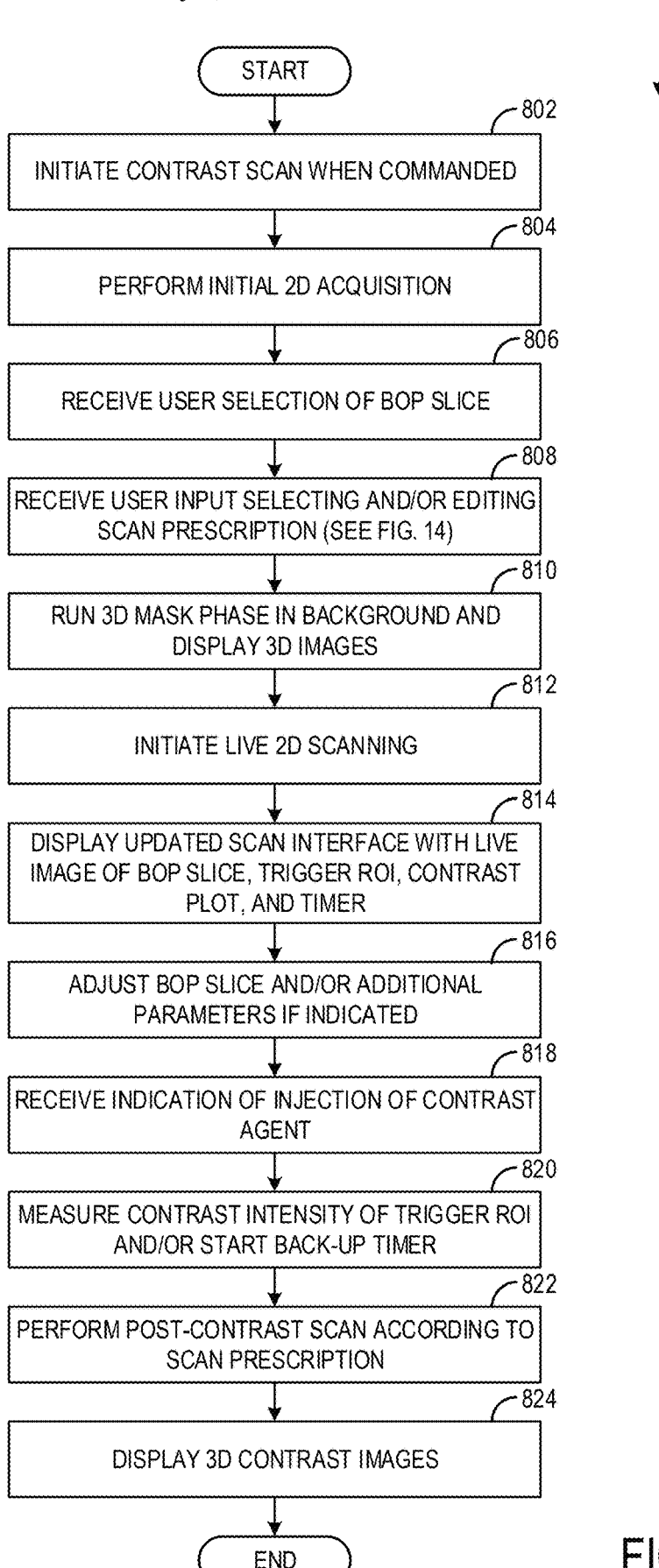
FIG. 8 is a high-level flow chart of a method for a contrast scan, according to embodiments of the disclosure.

FIG. 8 is a flowchart illustrating a high-level method 800 for a contrast scan, according to an embodiment of the disclosure. Method 800 may be implemented with the scan control device 202 of FIG. 2 in conjunction with the MRI apparatus 10 of FIG. 1. Method 800 may be carried out according to instructions stored in non-transitory memory and executed by a processor, such as non-transitory memory 206 and processor 204 of scan control device 202 of FIG. 2. The contrast scan performed according to method 800 may include events that occur before injection of a contrast agent to an imaging subject, as well as events that occur after the injection. Thus, the contrast scan may include pre-contrast actions (e.g., pre-contrast image acquisitions that include acquisition of MR images before administration of contrast agent and/or before the contrast agent reaches a level for post-contrast imaging) and post-contrast actions (e.g., post-contrast image acquisitions that include acquisition of MR images after the contrast agent reaches the level for post-contrast imaging).

At 802, the contrast scan is initiated when commanded. For example, the contrast scan may be initiated in response to a user selection of a "Scan" button displayed on a display device. Once an operator of the MRI apparatus has been authenticated, a scan protocol interface may be displayed wherein the operator may indicate that a contrast scan is to be carried out on an imaging subject. In some examples, via the scan protocol interface, the operator may select a specific contrast-enhanced scan protocol, such as a 3D LAVA multi-phase scan, enter information about the imaging subject, etc. When the operator is ready to initiate the scan (e.g., the imaging subject is in the bore of the MRI apparatus), the operator may select the Scan button, which may both trigger initiation of the scan and cause a scan interface to be launched.

At 804, an initial 2D acquisition is performed. As explained above with respect to FIG. 3, the scan protocol may include a prescan phase followed by an initial 2D acquisition. The images from the initial 2D acquisition may be viewed via the scan interface.

At 806, user selection of a BOP slice (e.g., contrast observation slice) is received. The BOP slice may be the slice that optimally visualizes an anatomical feature, such as a vessel, that is to be observed during contrast uptake for triggering the start of the post-contrast acquisitions. For example, as explained above with respect to FIG. 4, the user (e.g., the operator of the MRI apparatus) may place a respective box/rectangle over each image displayed in the prescription view of the scan interface following the initial 2D acquisition in order to select the BOP slice.

At 808, method 800 includes receiving user input selecting and/or editing a scan prescription for the contrast scan. The scan prescription may be selected and/or edited by the user via a scan prescription display panel of the scan interface, in some examples. As explained above, the scan prescription display panel may present the scan prescription in a timeline format or a table format, each of which may be edited by the user to select the number of post-contrast 3D acquisition phases, the delays before each phase, whether or not 3D mask images are acquired, and the like. Once the user selects/edits the scan prescription, the user may save the scan prescription via a save button of the scan interface and the contrast scan will be carried out according to the selected/edited scan prescription. Additional details about the scan prescription display panel and setting the scan prescription via the scan prescription display panel are presented below with respect to FIGS. 10-14. Thus, the scan control device may be configured to display, via the prescription view of the scan interface, the scan prescription display panel including an editable timeline, and the scan control device may be configured to set a scan prescription for one or more post-contrast acquisitions via user input to the editable timeline. As will be explained in more detail below, the scan control device may be further configured to display, via a live scanning view of the scan interface, a visualization of the scan prescription in the scan prescription display panel and carry out the one or more post-contrast acquisitions according to the scan prescription (e.g., as set via the scan prescription display panel).

After the initial 2D acquisition is performed, the scan protocol may include a 3D mask phase wherein 3D mask images are acquired. Thus, method 800 includes, at 810, running a 3D mask phase in the background (e.g., while the user is selecting the BOP slice) and, as the 3D mask images are reconstructed, displaying the 3D mask images. The 3D mask images may be displayed on an interface that is different from the scan interface.

At 812, method 800 includes initiating live 2D scanning. The live 2D scanning may be initiated in response to user input, e.g., in response to user selection of a Start Live Scan button of the scan interface. During the live 2D scanning, "live" images of the BOP slice are obtained, e.g., the MRI apparatus obtains MR signals in a continuous manner to facilitate reconstruction of low resolution, 2D images of the BOP slice, which are displayed in real-time (e.g., without any intentional delay) as the 2D images are reconstructed.

At 814, an updated scan interface is displayed (e.g., the live scanning view of FIG. 5), with a constantly-updating live 2D image of the BOP slice, a trigger ROI placed on the live 2D image, a contrast plot, and a back-up timer included in the updated scan interface. For example, the scan interface displayed while the user selects the BOP slice and/or selects/edits the scan prescription may be the prescription view of the scan interface illustrated in FIG. 4, and the updated scan interface may be the live scanning view of the scan interface illustrated in FIG. 5. The updated scan interface may be displayed in response to user selection of a user interface button, such as a Start or Scan button of the scan interface, and live scanning may commence in response to user selection of another user interface button, such as a Start Live Scan button on the scan interface. The trigger ROI is a region of the BOP slice selected for measuring the contrast level and may be visually indicated on the scan interface via a trigger marker placed on the live 2D image. The scan interface includes a contrast tracking display panel that includes the contrast plot and back-up timer. Before injection of the contrast agent, the contrast plot may be blank (e.g., no curve/graph displayed) and the back-up timer may be at zero/not yet triggered.

At 816, method 800 includes adjusting the BOP slice and/or one or more additional parameters if indicated (e.g., if requested by the user). As explained above, the user may move the BOP slice (e.g., in an anterior/posterior direction, medial/lateral direction, or proximal/distal direction) via BOP movement elements such as arrows placed on the scan interface, in order to select the BOP slice that sufficiently visualizes the trigger ROI. If the user adjusts the BOP slice, the scanner may be commanded to change the slice that is imaged during the live 2D scanning. The user may adjust other parameters as well, as such as changing the location of the trigger ROI, or enabling or disabling auto-triggering, the back-up timer, image subtraction, or saturation. If the user has indicated that a new baseline image is to be acquired (e.g., because the BOP slice (and the available adjustment slice) does not include the correct anatomy), the user may exit the live scanning view and re-prescribe from the beginning steps of the procedure (e.g., via the prescription view).

At 818, method 800 includes receiving an indication that an injection of a contrast bolus of contrast agent to the imaging subject has been initiated. As a non-limiting example, the contrast agent may comprise a gadolinium-based contrast agent. As other examples, the contrast agent may comprise a manganese-based contrast agent, an iron oxide contrast agent, or another suitable contrast agent. The contrast agent may be intravenously injected using either automatic or manual methods. The injection may be a contrast bolus for the contrast scan and, in some examples, may be the only contrast injection performed for the contrast scan (e.g., a separate timing bolus may not be administered). The indication that the injection has commenced may be received via user selection of a Monitor Injection button on the scan interface.

At 820, method 800 includes measuring the contrast intensity of the trigger ROI and/or starting the back-up timer. For example, if the user has enabled the back-up timer, the back-up timer may begin to increment upwards once the injection of contrast agent begins. Further, the live 2D images of the BOP slice may be analyzed to measure the contrast intensity. For example, the average brightness/intensity of the pixels of the trigger ROI in each live 2D image may be calculated and plotted as a function of time or image number, with the resultant curve displayed in the contrast plot of the scan interface. The curve may be updated with each live 2D image, and thus may be a live curve.

At 822, the post-contrast portion of the contrast scan (e.g., post-contrast 3D acquisitions, also referred to as the post-contrast scan) is performed according to the scan prescription. In some examples, the post-contrast scan may be triggered responsive to the measured contrast intensity of the trigger ROI reaching a threshold intensity. In other examples, the post-contrast scan may be triggered responsive to user selection of a Start Contrast Scan button of the scan interface, and the user may select the Start Contrast Scan button in response to visually determining that the contrast level in the trigger ROI is at a desired level for the post-contrast scan. In still further examples, the post-contrast scan may be triggered responsive to the back-up timer reaching a threshold time. The post-contrast scan may include a first delay, where no image acquisition takes place, after the post-contrast scan be triggered. After the first delay, the first phase of the post-contrast scan may be carried out by the scanner. The first phase may include a specified pulse sequence(s) being played out by the scanner to acquire MR signals suitable for reconstructing 3D contrast images, for example. In some examples, the post-contrast scan may include multiple phases, each separated by a specified delay and/or pause in scanning.

At 824, the 3D contrast images are displayed. The 3D contrast images may be displayed in a different/separate interface than the scan interface, at least in some examples. In this way, the post-contrast 3D images may not be displayed in the scan interface. In some examples, the separate/different interface that displays the 3D contrast images may be displayed on a separate display device, or the interface may be displayed on the same display device as the scan interface, but in a different window. Further, the 3D contrast images may be saved in memory. In some examples, the 3D contrast images may be saved at least temporarily in memory of the scan control device and may be sent to an image archive (e.g., PACS) for long-term storage. Method 800 then ends.

Figure 9A:
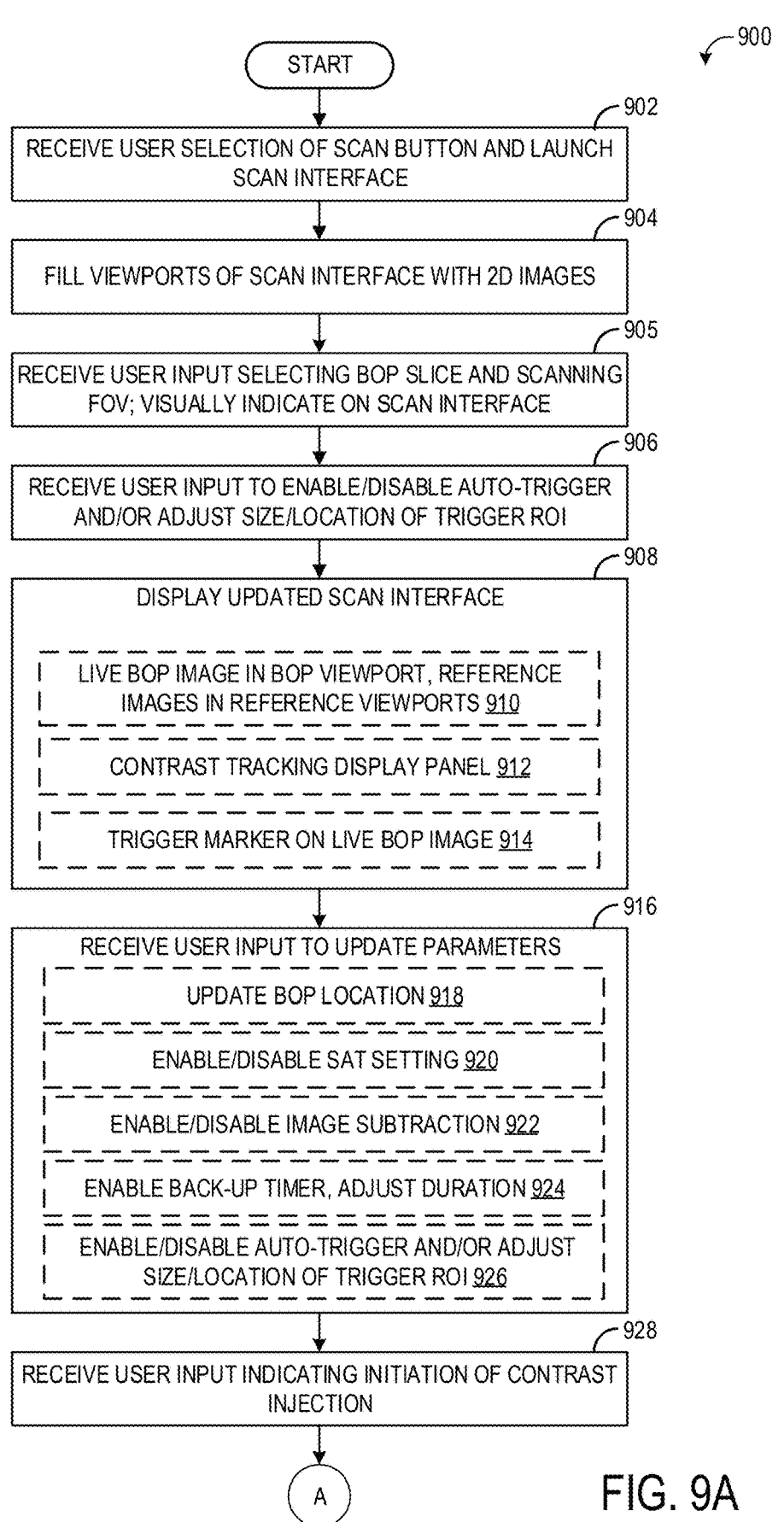
FIGS. 9A and 9B show a flow chart illustrating a method for a scan interface during the contrast scan, according to embodiments of the disclosure.
Figure 9B:
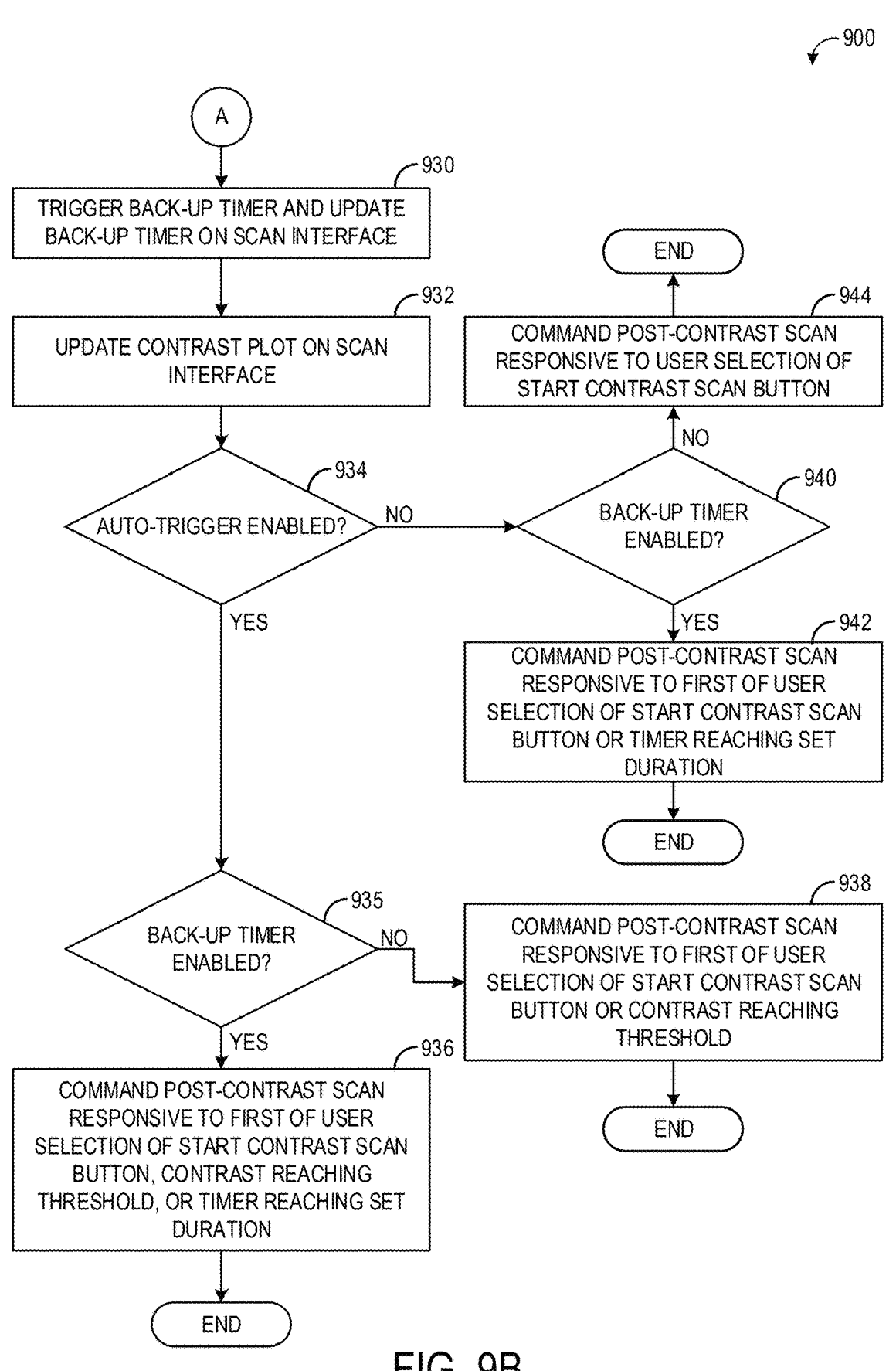

FIGS. 9A and 9B are a flowchart illustrating method 900 for a scan interface, according to an embodiment of the disclosure. Method 900 may be implemented with the scan control device 202 of FIG. 2 in conjunction with the MRI apparatus 10 of FIG. 1. Method 900 may be carried out according to instructions stored in non-transitory memory and executed by a processor, such as non-transitory memory 206 and processor 204 of scan control device 202 of FIG. 2. In some examples, method 900 may be a more granular method for carrying out the contrast scan of method 800 that specifically includes the user interaction with the scan interface and actions of the scan control device taken in response to the user interaction with the scan interface.

At 902, method 900 includes receiving a user selection of a Scan button and launching the scan interface. As explained previously, the scan interface may be launched in response to a user request to view the scan interface, such as user selection of a "Scan" button displayed on a display device. When launched, the scan interface may be displayed on the display device. The request to view the scan interface may also include a request to initiate the contrast scan. As explained above, the user may indicate, prior to launching of the scan interface, that a contrast scan of a particular protocol (e.g., multi-phase 3D contrast scan) is to be carried out on an imaging subject and may begin the contrast scan after the imaging subject is positioned in the bore of the MRI apparatus. Once the user indicates that the contrast scan is to begin, the scan interface may be launched and displayed on a display device (e.g., display device 234). Once the contrast scan begins, initial 2D images of the imaging subject may be acquired (e.g., after a prescan phase where the MRI apparatus is calibrated for the imaging subject).

At 904, the viewports of the scan interface are filled with the initial 2D images. When the scan interface is initially displayed with the initial 2D images, the scan interface may be in the prescription view, as shown in FIG. 4. In some examples, the initial 2D images may include images of a field of view of the imaging subject (e.g., centered at an isocenter of the bore of the MRI apparatus) in three views/planes, such as axial, coronal, and sagittal. Thus, a set of initial 2D images of the imaging subject may be displayed in the prescription view of the scan interface. At 905, method 900 includes receiving user input selecting a BOP slice and a scanning field of view (FOV), and visually indicating the BOP slice and scanning FOV on the scan interface. As explained above with respect to FIG. 4, once the initial 2D images are displayed via the scan interface, the user may place, move, and/or resize a first box/rectangle and a second box/rectangle to indicate the desired scanning FOV and BOP slice, respectively. The first and second boxes/rectangles are displayed over the initial 2D images to indicate the extent of the scanning FOV and the position of the BOP slice in each of the three image planes (e.g., axial, coronal, and sagittal). Accordingly, via the prescription view of the scan interface, a user selection of a contrast observation slice (e.g., the BOP) may be received.

At 906, method 900 includes receiving user input to enable or disable auto-triggering and/or to adjust the size and/or location of a trigger ROI. In some examples, after the user has selected the BOP slice and scanning FOV (and after the user has completed/selected the scan prescription), the scan interface may be updated to the live scanning view shown in FIG. 5, but without the live 2D images populated in the viewports. In such examples, the scan interface includes the auto-triggering button for enabling and disabling auto-triggering (e.g., as part of the contrast tracking display panel). As such, the user may enter user input to the auto-triggering button to enable or disable auto-triggering. Further, in some examples, once auto-triggering is enabled, a trigger marker may be placed at least onto the image in the BOP viewport to indicate the location of the trigger ROI for contrast measurement. The trigger marker may initially be placed in a default location (e.g., in the center of the BOP viewport) and may be moved and/or resized by the user to update the location/size of the trigger ROI. Accordingly, via the prescription view of the scan interface, a user selection of a trigger ROI may be received.

At 908, an updated scan interface is displayed. In some examples, a user selection of a start button or a scan button on the prescription view may trigger display of the updated scan interface. In some examples, a user selection of a live scan button (e.g., the Start Live Scan button shown in FIG. 5) may trigger live 2D scanning. The updated scan interface may be the live scanning view shown in FIG. 5. Accordingly, in response to a user input (e.g., selection of a start button or scan button displayed on the prescription view), a live scanning view of the scan interface that includes a viewport for displaying a live 2D image of the contrast observation slice and a contrast tracking display panel may be displayed. Thus, the updated scan interface that is displayed during the live 2D scanning may include, as indicated at 910, a live BOP image in the BOP viewport and orthogonal reference images in the reference viewports. The live BOP image may be a live (e.g., constantly updating) image of the selected BOP slice and the BOP viewport may be the larger, central, main viewport, while the reference images may be in the planes orthogonal to the live BOP image and the reference viewports may be the smaller, off-center viewports. As such, the live 2D image in the BOP viewport may be updated as new live 2D images are received. Further, as indicated at 912, the updated scan interface may include a contrast tracking display panel that includes a contrast plot, which is an area where a live contrast curve (e.g., of measured contrast intensity plotted as a function of time) relative to a threshold will be displayed once the contrast agent is administered to the imaging subject and travels to the trigger ROI. The contrast tracking display panel further includes a back-up timer button that can be selected to enable to disable the back-up timer, which is visually presented in the contrast tracking display panel. The updated scan interface may further include the trigger marker on the live BOP image, as indicated at 914.

At 916, method 900 includes receiving user input to update one or more parameters. For example, the BOP slice location may be updated, as indicated at 918. As shown in FIG. 5, a line may be placed over the reference images in the reference viewports that shows the location of the BOP slice, and the BOP slice may be moved in increments via arrows on either side of the line. As another example, a saturation (SAT) setting may be enabled or disabled responsive to user input to a saturation button of the scan interface, as indicated at 920. When the SAT setting is enabled, each live 2D image of the contrast observation slice is acquired with a saturation pulse sequence. Further, image subtraction may be enabled or disabled responsive to user input to a subtraction button of the scan interface, as indicated at 922. Both the saturation setting and image subtraction impact the contrast/visual quality of the live BOP image. Specifically, saturation, when enabled, may suppress the signal from adipose tissue and enhance visualization of the contrast agent. Image subtraction may include the subtraction of a non-contrast image (e.g., a BOP image acquired before administration of the contrast agent) from a contrast image (e.g., a BOP image acquired after administration of the contrast agent), which may also help visualization of the contrast agent.

As still further examples of parameters that may be adjusted via user input to the scan interface, the back-up timer may be enabled or disabled via user input to/at the back-up timer button, and the duration of the back-up timer may be set or adjusted via input to a timer duration menu, for example, as indicated at 924. Further, as indicated at 926, the auto-triggering may be enabled or disabled during the live 2D scanning, which may be performed as explained above. Additionally, the threshold contrast intensity for triggering the post-contrast scan may be adjusted via input to the scan interface (e.g., via dragging the threshold displayed on the contrast plot of the contrast tracking display panel). Likewise, the size or location of the trigger ROI may be adjusted during live 2D scanning, for example by moving the trigger marker or entering input to a trigger marker button or menu.

At 928, method 900 includes receiving user input indicating the initiation of contrast injection. As explained previously, once the injection of the contrast bolus of contrast agent has begun, the user may select the Monitor Injection button on the scan interface, which may signal to the scan control device that the contrast agent has been administered to the imaging subject. As a result, the back-up timer may be triggered (if enabled), and the time indicated by the back-up timer may be updated on the scan interface, as indicated at 930 of FIG. 9B. Specifically, once the Monitor Injection button is selected, the back-up timer may begin counting upwards and this is reflected on the timer displayed in the contrast tracking display panel. The live 2D scanning continues and the obtained live 2D images (the BOP images, of the BOP slice) may be evaluated to measure the contrast intensity in the trigger ROI. Thus, at 932, method 900 includes updating the contrast plot on the scan interface. The contrast plot may include a live curve (e.g., as shown in FIG. 7) depicting contrast intensity in the trigger ROI as a function of time, and the live curve may be updated at a suitable rate (e.g., with each new 2D acquisition). Thus, responsive to receiving a user input indicating injection of a contrast agent to the imaging subject has begun, a live curve plotting measured contrast intensity of the trigger ROI as a function of time since the injection may be displayed in the contrast tracking display panel, while continuing to update the live 2D image of the contrast observation slice in the BOP viewport.

At 934, method 900 determines if auto-triggering has been enabled (e.g., if the auto-triggering button is in the on position). If auto-triggering has been enabled, method 900 proceeds to 935 to determine if the back-up timer has been enabled (e.g., if the timer button is in the on position). If the back-up timer has been enabled, method 900 proceeds to 936 to command initiation of the post-contrast scan responsive to a first of user selection of the start contrast scan button, the measured contrast intensity reaching the threshold intensity, or the back-up timer reaching the set duration. In this way, the post-contrast scan may be initiated once the measured contrast level reaches the threshold intensity. However, if the contrast intensity does not reach the threshold intensity before the set duration of the back-up timer is reached, the post-contrast scan may be triggered responsive to the back-up timer reaching the set duration. Further, the post-contrast scan may be triggered responsive to user input, e.g., selection of a Start Contrast Scan button of the scan interface. As such, the post-contrast scan may be initiated responsive to whichever of the user selection of the start contrast scan button, contrast level reaching the threshold intensity, and the back-up timer reaching the set duration happens first. If, at 935, it is determined that the back-up timer is not enabled, method 900 proceeds to 938 to command initiation of the post-contrast scan responsive to the first of the user selection of the start contrast scan button or the contrast level reaching the threshold intensity. It is to be appreciated that even when the back-up timer is not initiated, the timer may still be displayed on the scan interface to aid the user in determining whether or not to select the start contrast scan button to initiate the post-contrast scan.

Returning to 934, if it is determined that auto-triggering has not been enabled, method 900 proceeds to 940 to determine if the back-up timer is enabled. If the back-up timer is enabled, method 900 proceeds to 942 to command initiation of the post-contrast scan responsive to the first of user selection of the Start Contrast Scan button of the scan interface or the back-up timer reaching the set duration. Thus, if the user does not select the Start Contrast Scan button before the set duration of the back-up timer is reached, the post-contrast scan may be triggered responsive to the back-up timer reaching the set duration. If the back-up timer is not enabled, method 900 proceeds to 944 to command initiation of the post-contrast scan responsive to user selection of the Start Contrast Scan button of the scan interface, regardless of the duration of the back-up timer.

In this way, the post-contrast scan may be triggered by any one of three triggers, according to which trigger(s) is enabled and which trigger occurs first. For example, the scan control device may command initiation of one or more post-contrast acquisitions responsive to any of the live curve reaching a threshold intensity, a user input being received indicating that the post-contrast scan is to commence, and the back-up timer reaching a threshold duration (e.g., depending on which happens first in time and whether or not the auto-triggering and/or the back-up timer are enabled). In an example, if the auto-triggering button of the scan interface is in the on position (e.g., auto-triggering is enabled) and the back-up timer button of the scan interface is in the on position (e.g., the back-up timer is enabled), the scan control device may command initiation of the one or more post-contrast acquisitions responsive to the live curve reaching the threshold intensity unless a user selection of the start contrast scan button is received before the live curve reaches the threshold intensity or unless the back-up timer reaches the threshold duration before the live curve reaches the threshold intensity. In another example, if auto-triggering is not enabled and the back-up timer is enabled, the scan control device may command initiation of the one or more post-contrast acquisitions responsive to user selection of the start contrast scan button unless the back-up timer reaches the threshold duration before the user selection of the start contrast scan button is received. Method 900 then ends.

As explained previously, a user (e.g., an operator of an MRI apparatus) may set various aspects of a contrast scan to be carried out on an imaging subject (e.g., a patient), referred to as a scan prescription. For a contrast scan, the scan prescription may dictate the number of phases of image acquisition (e.g., generation and collection of MR signals that are reconstructed into images) to be performed after the contrast agent has reached a desired level at an anatomical feature (e.g., vessel) and the delays, if any, between the phases. For example, each phase may be timed to acquire images during a particular phase of contrast uptake and washout, such as arterial, venous, delayed, etc., and the delays may be set to ensure imaging occurs during the prescribed contrast phases and/or allow for patient recovery between breath holds. As different patients exhibit different contrast kinetics (e.g., the amount of time for the contrast agent to travel from the injection site to the vessel and for the contrast agent to progress through the various contrast phases before being washed out) due to patient age, size, heart conditions (e.g., arterial fibrillation), and so forth, different patients may demand different scan prescriptions even for the same type of contrast scan/goal of the contrast scan.

Typically, to set the scan prescription, a user may select the number of phases, set the delays between phases, and set other parameters via a series of menus, numerical input boxes, and checkboxes presented on one or more display panels. During setting/editing of the scan prescription, little to no visualization of a default scan prescription, or the scan prescription as set by the user (to that point) is generally provided. As such, the user has to build a sequence of events for the scan prescription using various input parameters, without any visual cues about what the user is building, thus forcing the user to build and remember the scan prescription entirely "in their head." Further, once the scan prescription is set, typical methods may present a crude timeline of the phases, but typically the timeline cannot be directly edited. As such, if the user determines, upon viewing the timeline, that a set delay is not accurate, the user must go back to the original display panel and edit the specific delay setting, if such a modification is even allowed at that point (e.g., once the scan prescription settings have been saved).

Thus, as explained previously, the scan interface disclosed herein may include a scan prescription display panel that may include various user interface elements (e.g., buttons, tiles, menus) for setting a scan prescription for a contrast scan in a timeline format or a table format, wherein the scan prescription can be visualized as a timeline both during setting of the scan prescription and once the scan prescription is set (e.g., including during execution of the contrast scan). The timeline can be directly edited via simple and intuitive buttons and drag-and-drop capabilities. Further, any additions or edits to the scan prescription made via the timeline format may be automatically populated into a table and the user may view the table, if desired, and make changes/additions to the scan prescription via the table. Likewise, if the user makes additions/edits to the scan prescription via the table, the additions/edits will be populated into the timeline. In this way, the scan prescription display panel may provide the user a simpler, more human, way to interact with the complexities happening in the backend of the MRI apparatus.

FIG. 10 shows an example scan prescription display panel 1000 in an editable timeline view 1001. The scan prescription display panel 1000 may be a non-limiting example of the scan prescription display panel 414 of FIGS. 4 and 5, and thus may be included as part of the scan interface disclosed herein (e.g., as part of the scan interface shown in FIGS. 4-6). However, the scan prescription display panel 1000 may be included in other interfaces, or as a stand-alone interface, without departing from the scope of this disclosure. Further, while the scan prescription display panel is described herein as being used to set the scan prescription for a contrast scan with an MRI system, it is to be appreciated that a similar scan prescription display panel may be used to set the scan prescription for other types of scans, such as contrast-enhanced computed tomography (CT) scans.

The scan prescription display panel 1000 includes a timeline button 1002 and a table button 1004. When the timeline button 1002 is selected, the timeline view 1001 is displayed. When the table button 1004 is selected, an editable table view is displayed (shown in FIG. 12 and described in more detail below). The timeline button 1002 has been selected in the example shown in FIG. 10, and thus the timeline button 1002 is emphasized relative to the table button 1004.

In the editable timeline view 1001, the scan prescription display panel 1000 includes an add mask button 1006, an add injection button 1008, and an add phase button 1010. The add mask button 1006 is selectable to add a mask step (e.g., a pre-contrast, 3D mask imaging step) to the scan prescription. The add injection button 1008 is selectable to add an injection step (e.g., whereby contrast is injected to the imaging subject) to the scan prescription. The add phase button 1010 is selectable to add an imaging phase (e.g., a post-contrast imaging phase) to the scan prescription. Further, the scan prescription display panel 1000 in the editable timeline view 1001 includes a total phase menu 1012. The total phase menu 1012 may include arrows that are selectable to increase or decrease the total number of post-contrast imaging phases of the scan prescription. The add phase button 1010 may allow the operator to add one phase at a time to the scan prescription, while the total phase menu 1012 may allow the operator to add or remove multiple phases at a time to the scan prescription, thereby allowing the operator to add or remove one or multiple phases with a single input. Additionally, the scan prescription display panel 1000 in the editable timeline view 1001 includes a step removal area 1014. Any step that has been added to the scan prescription may be removed by dragging that step from the timeline and dropping the step in the step removal area 1014, as described below.

As each desired step is added to the scan prescription, the step may be visualized via a timeline 1020. Thus, each step may be visualized in temporal order relative to each other step of the scan prescription, as the scan prescription is being generated. For example, in response to user selection of the add mask button 1006, a mask tile 1022 is added to the timeline 1020 and the scan prescription is updated to include a mask image acquisition step. Likewise, in response to user selection of the add injection button 1008, an injection tile 1024 is added to the timeline 1020 and the scan prescription is updated to indicate that an injection of contrast agent will be performed after the mask image acquisition step. In some examples, a first delay tile 1026 may be added to the timeline 1020 along with the injection tile 1024. The first delay tile 1026 may indicate a first delay, in seconds, between when the scan control device or user determines that the contrast agent in the anatomy of interest in the imaging subject is at the preferred level for initiating the post-contrast acquisitions and when the first post-contrast acquisition begins. The scan prescription may be updated to indicate the first delay following the injection step.

Further, in the example shown, the user has indicated, via the total phase menu 1012, that the scan prescription is to include a total of four phases of post-contrast image acquisition. As a result, the scan prescription is updated to include four phases and the timeline 1020 is auto-filled with tiles for each of the four phases, such as a first phase tile 1028. The tiles for the first three phases may include a corresponding delay tile, such as a second delay tile 1030, that indicates the delay, in seconds, between phases. For example, the second delay tile 1030 may indicate the delay between when the first phase ends and the second phase begins.

The user may edit the scan prescription via the timeline 1020. As such, the timeline 1020 shown in FIG. 10 may be an editable version of the timeline 1020. For example, to set or change a delay, the user may select an input box of that delay tile and enter input (e.g., via a keyboard) to set or change the delay time, which is then reflected in the scan prescription. For example, the first delay tile 1026 shows an input box 1027 that can be selected in order to edit the number of seconds for the first delay. The phase tiles may also include input boxes that can be edited to name each phase (e.g., arterial, venous, etc.). The phase tiles may further include an automatically-calculated duration for that phase based on the pulse sequence(s) to be carried out during that phase. For example, the first phase tile 1028 may include a duration of 15 seconds, which indicates that the first phase of post-contrast scanning may have a duration of 15 seconds. If the user decides that a previously-added step/phase should be removed from the scan prescription, the user may drag the associated tile to the step removal area 1014 to delete that step/phase. For example, as shown, the user is dragging a tile 1032 for the second phase from the timeline 1020 to the step removal area 1014 to delete the second phase, which may trigger the phases following the second phase to be renumbered (e.g., phase three becomes phase two, etc.). Further, steps/phases may be reordered by dragging the associated tile to the desired location. For example, rather than deleting the second phase, the user may instead move the tile 1032 to between the third phase and the fourth phase.

The timeline 1020 may further include a time marker 1034 that begins at the end of the injection step (e.g., when the post-contrast scan will be officially initiated, such as when the user selects the start contrast scan button) and increments upward, in seconds, until the end of the final phase. Time points of interest may be marked on the time marker 1034, such as the time since the start of the post-contrast scan to the start of each phase. For example, the time marker 1034 includes a first time point of 0 at the end of the injection step, a second time point of 65 at the start of the first phase, a third time point of 136 at the start of the second phase, etc. The time points of the time marker 1034 may be calculated based on the duration of each phase and delay. For example, the first phase may have a duration of 15 seconds and the second delay following the first duration may be 56 seconds, and thus the third time point (e.g., 136) may be based on the first delay (of 65 seconds), the first phase (of 15 seconds), and the second delay (of 56 seconds). The time marker 1034 may include a label 1035 to indicate that the time depicted via the time marker 1034 is for the post-contrast scanning portion of the scan prescription. While not shown in FIG. 10, it is to be appreciated that the scan prescription display panel 1000 in the editable view may include a save button (e.g., the save button 419 of FIG. 4) that is selectable to save all the additions/changes to the scan prescription, so that the contrast scan can be carried out according to the scan prescription.

In some examples, the tiles may include icons or other visual indicators of the functionality that is to be performed at that step of the scan prescription. For example, the mask tile 1022 may include an icon of a mask, the injection tile 1024 may include an icon of a needle, and the delay tiles may each include an icon of a clock/timer. Further, each delay tile may include a numeric indicator of the number of seconds of that delay. In this way, the user may be able to easily differentiate the various steps of the scan prescription and view the delay associated with each step, all from the same timeline, even as the scan prescription is still being set.

FIG. 11 shows a second example editable timeline view 1101 of the scan prescription display panel 1000. The second example editable timeline view 1101 may depict a scan prescription that may be set for a contrast scan carried out according to the methods of FIGS. 8 and 9A and 9B. As such, some of the tiles may be auto-filled, such as a live scan slice tile 1102 and a monitor injection tile 1106, which may act as placeholders/reminders to the user of the actions occurring during those parts of the contrast scan. The timeline 1020 further includes a live scanning tile 1104 that indicates that the scanner will be in the live scanning mode showing the live 2D images prior to the Monitor Injection step being performed (e.g., prior to the user selecting the Monitor Injection button to initiate the contrast tracking). In the second example editable timeline view 1101 shown in FIG. 11, the scan prescription includes a first delay indicated by a first delay tile 1108, a first phase (denoted as the arterial phase) indicated by a first phase tile 1110, a second phase (portal venous phase) indicated by a second phase tile 1112, a second delay after the second phase indicated by a second delay tile 1114, and a third phase (delayed) indicated by a third phase tile 1116. The time marker 1034 additionally includes another label 1118 to indicate when the live scanning portion of the scan prescription occurs. It is to be appreciated that each phase has an associated delay following that phase, and the delay of the phase may be adjusted as described herein, including adjusting the delay to zero.

FIG. 12 shows the scan prescription display panel 1000 in an editable table view 1201. Specifically, FIG. 12 shows an editable table view of the second example editable timeline view 1101 of FIG. 11. As mentioned previously, the user may toggle from the second example editable timeline view 1101 to the editable table view 1201 by selecting the table button 1004. The scan prescription panel in the editable table view 1201 includes the add mask button 1006 and the add phase button 1010, as well as the total phase menu 1012. The editable table view 1201 further includes a table 1202 including a plurality of columns of cells. The plurality of columns includes a step column 1204, a start time column 1206, a duration column 1208, a delay column 1210, and a contiguous setting column 1212. Each column may include one or more cells.

The step column 1204 lists each step of the scan prescription that has been set/prescribed to that point. Thus, the step column 1204 includes a plurality of rows of cells, with each cell of the column filled with a prescribed step, including herein the mask step, the injection step, and the prescribed phases (e.g., the first, second, and third phases). The start time column 1206 includes cells that list the start time, from the start of the post-contrast scan (e.g., from when the user selects the start contrast button or from when the scan control device detects the contrast intensity has reached the threshold intensity or detects that the back-up timer has reached the set/threshold duration), of each phase. For example, as shown, the start of the first phase is 3 seconds, the start time of the second phase is 18 seconds, and the start time of the third phase is one minute, 13 seconds (e.g., 73 seconds). The duration column 1208 includes cells that list the duration of each step, which may be filled in automatically based on the pulse sequence that will be carried out.

The delay column 1210 includes cells that list the delay that is to occur after each step, before the next step commences. For example, a delay of 40 seconds is prescribed following the second phase, before the third phase commences. The contiguous setting column 1212 indicates if a pause is to be added between steps or not. It is to be appreciated that a pause has no set time and demands a user input to progress to the next step, whereas a delay has a set time and does not demand a user input to progress to the next step.

The scan prescription may be adjusted via direct edits to the table 1202. For example, at least some of the cells in some of the columns may be selected and edited via user input (e.g., via a keyboard). As shown, a cell 1214 in the delay column 1210 corresponding to the first phase has been selected and a user is entering a numeric value to set as the delay following the first phase. Further, the contiguous setting column 1212 may include contiguous icons, such as contiguous icon 1216, that may be activated or deactivated via user input. Each contiguous icon may span two cells to signal that the icon is for the pause between two adjacent steps, e.g., the contiguous icon 1216 spans the second phase and the third phase. When a contiguous icon is activated, a pause between steps is skipped and when a contiguous icon is deactivated, a pause is inserted between steps. In some examples, in response to a hover input over a contiguous icon, a pop-up display panel may be displayed, such as pop-up display panel 1218, providing guidance on the contiguous icons.

The scan prescription display panel in the editable table view 1201 includes additional buttons, such as injection button 1220, that may be selected to launch other display panels/interfaces. Further, in some examples, a pause may only be added or skipped via user input to the table 1202 (e.g., and not via the timeline). However, in some examples, the contiguous icon functionality may be incorporated on the timeline (e.g., a contiguous icon may be displayed between adjacent tiles on the timeline).

As shown in FIG. 13, once the scan prescription has been set (e.g., the user has selected the save button), the scan prescription display panel 1000 may switch to a scanning view 1301. The scanning view 1301 may be displayed during live scanning (including during contrast observation) and during the post-contrast scan (e.g., as shown in FIG. 5). The scanning view of the scan prescription display panel includes the timeline with a tile for each step of the scan prescription arranged in temporal order. The scanning view 1301 shown in FIG. 13 is the scanning view of the scan prescription shown in the second example editable timeline view 1101 and thus includes the steps prescribed as described above with respect to FIG. 12. As the contrast scan progresses and each step of the scan prescription is performed, the appearance of the corresponding tile on the timeline may be adjusted to indicate that the step has been performed. For example, as shown in FIG. 13, the mask tile 1022, pause tile 1104, monitor injection tile 1106, and first delay tile 1108 all include a checkmark to indicate those steps (e.g., the mask imaging step, pause, the monitor injection step, and the first delay) have been performed. The appearance of the current step of the scan prescription may also be adjusted to visually indicate the current step of the scan prescription. For example, the first phase tile 1110 is highlighted/in a different color relative to the other steps of the scan prescription. Steps that have yet to be performed, such as a second delay indicated by a second delay tile 1302, a second phase as indicated by a second phase tile 1304, etc., may be indicated via those tiles having a different visual appearance than the tiles corresponding to the steps that have already been performed and the current step.

Thus, a computing device (e.g., the scan control device 202) may include a display screen (e.g., display device 234), and the computing device may be configured to display on the screen a scan interface (e.g., scan interface 400) including a scan prescription display panel (e.g., scan prescription display panel 414 or scan prescription display panel 1000) in a timeline view (e.g. timeline view 1001 or 1101) including an editable version of a timeline, the scan prescription display panel in the timeline view configured to receive user input to enable a scan prescription of a contrast scan of an imaging subject to be set while displaying each step of the scan prescription via the editable version of the timeline as that step is set. The computing device may additionally be configured to display on the screen a button (e.g., scan button 422) that can be reached directly from the scan interface, wherein the button is selectable to initiate the contrast scan and launch a scanning view (e.g., scanning view 1301) of the scan prescription display panel that enables each step of the scan prescription to be seen via the timeline as the contrast scan is carried out. In some examples, the computing device is configured to save each step of the scan prescription and carry out the contrast scan according to the scan prescription (e.g., by commanding MRI apparatus 10 to carry out the contrast scan according to the scan prescription).

In some examples, the scan prescription display panel in the timeline view includes an add mask button (e.g., add mask button 1006) and an add phase button (e.g., add phase button 1010), and the computing device is configured to: add a mask step to the scan prescription and a mask tile (e.g., mask tile 1022) to the timeline in response to user selection of the add mask button; add a first phase and a first delay to the scan prescription and a first phase tile (e.g., first phase tile 1028) and a first delay tile (e.g., delay tile 1030) to the timeline in response to a first user selection of the add phase button; and add a second phase and a second delay to the scan prescription and a second phase tile and a second delay tile to the timeline in response to a second user selection of the add phase button. In some examples, the computing device is configured to adjust a duration of the first delay in response to user input to the first delay tile (e.g., in response to user input to the input box 1027). In some examples, the timeline in the scanning view of the scan prescription display panel includes the mask tile, an injection tile (e.g., injection tile 1024), the first phase tile, the first delay tile, the second phase tile, and the second delay tile and further includes a time marker (e.g., time marker 1034) depicting time points from an end of an injection step depicted by the injection tile to a start of the first phase and the second phase, respectively. In some examples, when the scan prescription display panel is in the scanning view, the computing device is configured to adjust a visual appearance of the mask tile responsive to the mask step being initiated, and further adjust a visual appearance of the mask tile responsive to the mask step being completed. In some examples, the computing device is configured to display on the screen the scan interface in a prescription view (e.g., prescription view 401), and further configured to receive user input via the scan interface in the prescription view to enable prescription of a contrast observation slice for tracking arrival of a contrast bolus during the contrast scan (e.g., via placement of the second box 412), and wherein the editable version of the timeline is displayed within the scan interface in the prescription view. In some examples, the computing device is additionally configured to display on the screen a scanning button (e.g., scan button 422) that can be reached directly from the scan interface in the prescription view, wherein the scanning button is selectable launch a live scanning view of the scan interface (e.g., live scanning view 501) that enables live 2D images of the contrast observation slice to seen within the scan interface, and wherein the scanning view of the scan prescription display panel is displayed within the live scanning view of the scan interface. In some examples, the live scanning view further includes a live scanning button (e.g., start live scan button 528) selectable to enable live 2D scanning of the contrast observation slice, and a contrast tracking display panel (e.g., contrast tracking display panel 510) that displays an auto-triggering button (e.g., auto-triggering button 512) that is selectable to enable auto-triggering of post-contrast image acquisition and enable a contrast intensity plot (e.g., live curve 702) determined from the live 2D images to be seen within the contrast tracking display panel.

Figure 14:
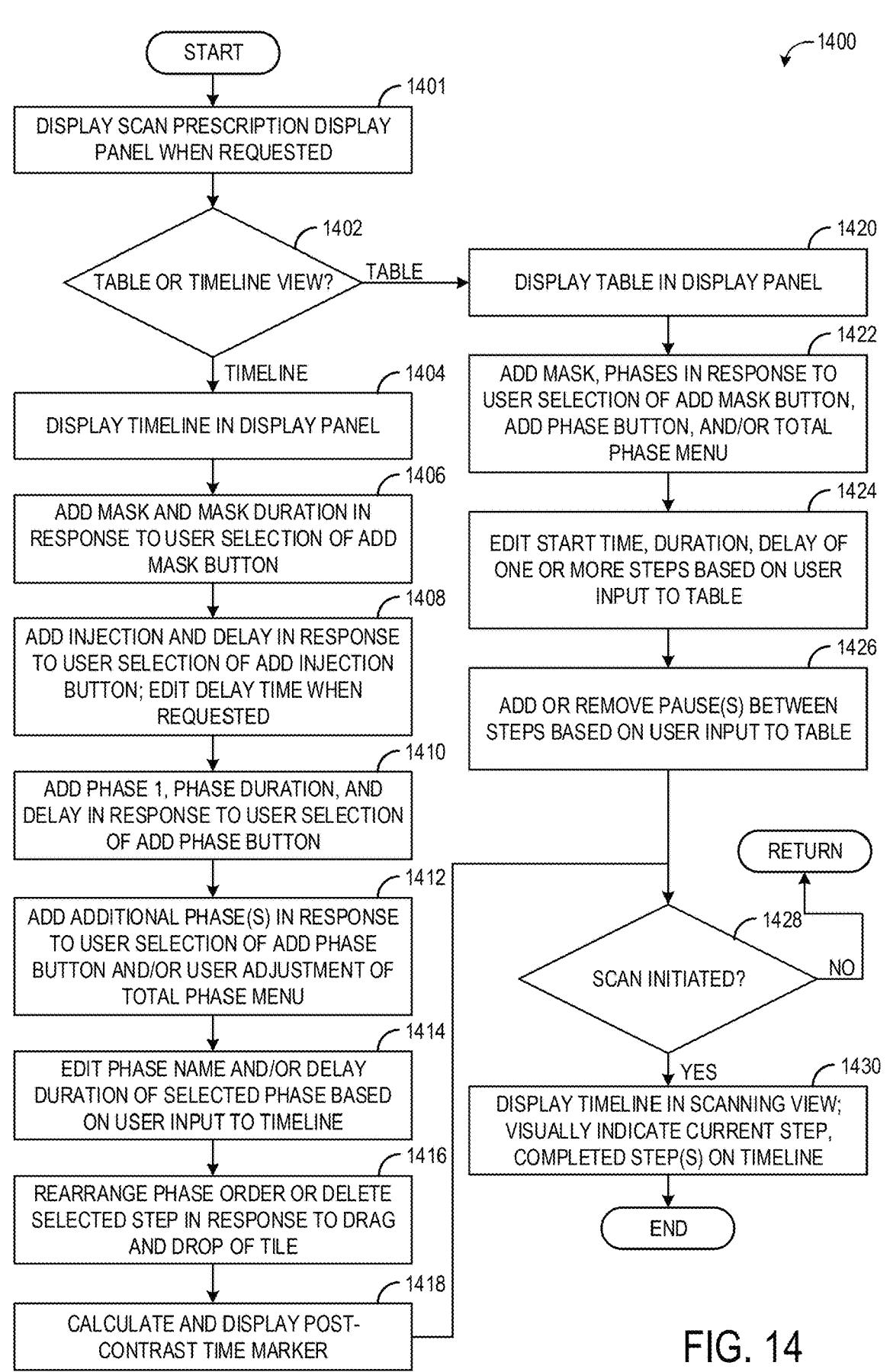
FIG. 14 is a flow chart illustrating an example method for setting a scan prescription via a scan prescription display panel.

FIG. 14 is a method for setting a scan prescription via a scan prescription display panel, according to an embodiment of the disclosure. Method 1400 may be implemented with the scan control device 202 of FIG. 2 in conjunction with the MRI apparatus 10 of FIG. 1. Method 900 may be carried out according to instructions stored in non-transitory memory and executed by a processor, such as non-transitory memory 206 and processor 204 of scan control device 202 of FIG. 2.

At 1401, method 1400 includes displaying the scan prescription display panel when requested. The scan prescription display panel may be displayed in response to user input requesting display of the scan interface of FIG. 4, and/or the scan prescription display panel may be displayed in response to user input requesting to set a scan prescription for a contrast scan to be carried out on an imaging subject. At 1402, method 1400 determines if the scan prescription display panel is in the table view or the timeline view, e.g., if the user has requested to view the table view or the timeline view. In some examples, the scan prescription may be displayed in the timeline view as a default and may only be displayed in the table view in response to user selection of a table button of the scan prescription display panel. Further, prior to commencement of the contrast scan, the scan prescription display panel may include an editable view of the timeline or table. However, before any steps of the scan prescription have been set, the scan prescription display panel may be in the timeline view (or table view) but the editable version of the timeline (or table) may not yet be displayed. For example, referring to FIG. 10, initially only the add mask button 1006, the add injection button 1008, the add phase button 1010, the total phase menu 1012, and the step removal area 1014 may be displayed, along with the timeline button 1002 and the table button 1004.

If the scan prescription is in the timeline view and/or the user requests to view the scan prescription in the timeline view, method 1400 proceeds to 1404 to display an editable version of a timeline in the scan prescription display panel in response to a first user input specifying a step of the scan prescription. Before the scan prescription has been built, and thus when the timeline is initially displayed, the timeline may be blank or not displayed at all. In other examples, when the timeline is initially displayed, the timeline may be auto-filled with one or more steps based on a selected scan protocol. For example, before the contrast scan begins, the user (e.g., the operator of the MRI apparatus) may enter user input specifying or selecting a scan protocol. The scan protocol may dictate the anatomy being scanned (e.g., the liver), whether the imaging subject is an adult or child, the diagnostic goal of the contrast scan, and the like, which may dictate to the scan control device which types of pulse sequences will be carried out to acquire the images as set forth in the scan protocol. Depending on the selected scan protocol, some steps of the scan prescription may be selected automatically, such as selection of the live scanning slice, monitoring injection, one or more post-contrast image acquisition phases, etc.

At 1406, method 1400 includes adding a mask step (to the scan prescription and to the timeline) and optionally a duration of the mask step in response to user selection of an add mask button of the scan prescription display panel. For example, the add mask button 1006 of the scan prescription display panel 1000 may be selected, and in response, a mask tile (e.g., mask tile 1022) may be added to the timeline. Additionally, the mask step may be added to the scan prescription. At 1408, method 1400 includes adding an injection step (to the scan prescription and to the timeline) and a delay in response to user selection of an add injection button of the scan prescription display panel, and optionally editing the delay time when requested. For example, the add injection button 1008 of the scan prescription display panel 1000 may be selected, and in response, an injection tile (e.g., injection tile 1024) may be added to the timeline. Additionally, the injection step and delay may be added to the scan prescription. Further, the delay associated with the injection step may be set with a default duration (e.g., 15 seconds, 0 seconds) and the user may change the duration of the delay via user input to an input box of the injection tile, if desired.

At 1410, method 1400 includes adding a first phase (phase 1), phase duration, and delay (to the scan prescription and to the timeline) in response to user selection of an add phase button. For example, the add phase button 1010 of the scan prescription display panel 1000 may be selected, and in response, a first phase tile (e.g., first phase tile 1028) may be added to the timeline along with a delay tile (e.g., delay tile 1030). Additionally, the first phase and delay may be added to the scan prescription.

At 1412, method 1400 includes adding one or more additional phases in response to user selection(s) of the add phase button and/or in response to user adjustment of a total phase menu. Each time the user selects the add phase button, a new phase may be added to the timeline and scan prescription, and each new phase may include an associated delay. Alternatively, the user may set the total number of phases via the total phase menu (e.g., total phase menu 1012), and the corresponding number of phases may be added to the scan prescription and the timeline. Each added phase may have an associated delay other than the final phase of the scan prescription.

Thus, in some examples, responsive to a first user input (e.g., user selection of the add mask button, the add injection button, the add phase button, or adjustment to the total phases menu), the editable version of the timeline may be displayed that includes a first tile corresponding to a first step in the scan prescription. As additional user input is received, more tiles may be displayed in the editable version of the timeline and corresponding steps added to the scan prescription.

At 1414, method 1400 includes editing a phase name and/or a delay duration of a selected phase based on user input to the timeline. As explained above, each delay associated with a phase may be set with a default duration (e.g., 15 seconds, 0 seconds) and the user may change the duration of the delay via user input to an input box of the selected phase tile, if desired. Similarly, the user may select an input box associated with the name of the phase and change the name from the default name (e.g., phase 1) to a desired name (e.g., arterial phase).

At 1416, the order of the phases may be rearranged, or a selected step may be deleted, in response to a drag-and-drop of a tile. For example, a tile representing a first phase may be moved via the drag and drop to behind a tile representing a second phase, and in response, the second phase may become the first phase and the first phase may become the second phase. In another example, a tile may be moved to a step removal area of the scan prescription display panel, such as the step removal area 1014 of scan prescription display panel 1000, via the drag and drop, and in response, the step associated with that tile (e.g., the first phase) may be deleted from the scan prescription and the tile removed from the timeline.

At 1418, method 1400 includes calculating and displaying a post-contrast time marker. The post-contrast time marker (e.g., time marker 1034) may indicate the time since the start of the post-contrast scan (e.g., when the scan control device or the user indicates that the post-contrast acquisitions should begin) to each phase of the post-contrast scan. The post-contrast time marker may be positioned proximate to the tiles of the timeline, e.g., below the tiles of the timeline, and may be aligned with the tiles such that a time point is marked on the post-contrast time marker for each phase tile.

At 1428, method 1400 includes determining if the contrast scan has been initiated. For example, once the user has set the scan prescription, the user may select a save button of the scan prescription display panel or scan interface. Responsive to selection of the save button, the scan prescription display panel may be displayed on the scan interface in the scanning view, and the start of the contrast scan may be determined responsive to user selection of a scan button of the scan interface, or in response to another suitable input that informs the MRI apparatus to initiate the contrast scan. The contrast scan may begin with a prescan phase and then progress to the rest of the contrast scan as dictated by the scan prescription (e.g., initial 2D acquisition, mask imaging, live scanning and monitoring the injection, and the post-contrast scan acquisition phases). If it is determined that the scan has not yet been initiated, method 1400 returns to 1402 and continues to display the scan prescription display panel in the selected view (e.g., the table or timeline view) and edit/set the scan prescription as requested by the user. If it is determined that the contrast scan has been initiated, method 1400 proceeds to 1430 to display the scan prescription display panel on the scan interface in the scanning view (e.g., as shown in FIG. 13), and visually indicate the current step and completed step(s) of the scan prescription on the timeline. For example, once a step is completed, the tile of the timeline corresponding to that step may be visually altered to indicate the step is completed, such as placement of a checkmark on the tile. For the step currently being performed, the tile corresponding to that step may be visually altered to indicate the step is currently being performed, such as by highlighting the tile, changing the color of the tile, etc. Method 1400 then ends.

Returning to 1402, if it is determined that the scan prescription display panel is in the table view, or if the user has requested to view the table view, method 1400 proceeds to 1420 to display an editable table in the scan prescription display panel. Before the scan prescription has been built, and thus when the table is initially displayed, the table may be blank. In other examples, when the table is initially displayed, the table may be auto-filled with one or more steps based on a selected scan protocol, as explained previously. Depending on the selected scan protocol, some steps of the scan prescription may be selected automatically, such as selection of the live scanning slice, monitoring injection, one or more post-contrast image acquisition phases, etc.

At 1422, method 1400 includes adding a mask step and/or one or more post-contrast phases to the scan prescription in response to user selection of an add mask button, an add phase button, and/or a total phase menu. The add mask button, the add phase button, and the total phase menu may be the same as the add mask button, the add phase button, and the total phase menu of the timeline view. Further, when one of the add mask button, the add phase button, and the total phase menu is selected (or in the case of the total phase menu, adjusted/value changed), a corresponding row of cells may be added to the table. For example, as shown in FIG.

12, user selection of the add mask button 1006 may result in the "Mask" step being added to the step column 1204, along with the addition of corresponding cells in the remaining columns (e.g., start time, duration, delay, etc.). Further, in some examples, in the table view, the scan prescription display panel may also include an injection button that is selectable to add an injection step to the scan prescription and a corresponding injection row to the table.

At 1424, method 1400 includes editing one or more of a start time, duration, and delay of one or more selected steps based on user input to the table. As explained above with respect to FIG. 12, at least some of the columns of the table may include editable cells wherein the user may adjust the value in that cell (e.g., a delay duration for the mask step). At 1426, method 1400 includes adding or removing a pause(s) between steps based on user input to the table. As explained above with respect to FIG. 12, the table may include a contiguous step column that includes icons between steps that are selectable to activate or deactivate a pause between those steps, and the user may add/activate a pause or remove/deactivate a pause by selecting an appropriate icon.

At 1428, method 1400 determines if the contrast scan has been initiated, as explained above. When the contrast scan is initiated, the scan prescription display panel switches to the scanning view, which includes the timeline, as indicated at 1430. Thus, the timeline is depicted during scanning even if the scan prescription was set via the table view. Further, it is to be appreciated that at any time during the setting of the scan prescription, the user may toggle from the timeline view to the table view or from the table view to the timeline view. Any steps of the scan prescription that have been set prior to switching views may be populated into the current view. For example, if the user sets the mask step in the timeline view and then toggles to the table view, the table will be displayed with the mask step already added to the table.

A technical effect of a scan interface as disclosed herein is that both a live view of a contrast bolus reaching a target anatomical feature and a system-measured live curve of the intensity of the contrast in the target anatomical feature may be viewed on the same, single scan interface, which may allow an operator of an imaging system to simultaneously monitor contrast enhancement via the live view and live curve without having to switch interfaces or screens, access different menus, or the like. Further, by auto-triggering the start of the post-contrast scan via the live curve as well as auto-triggering the start of the post-contrast scan with a back-up timer, missed acquisitions at peak or post-peak contrast enhancement due to operator distraction or unusual patient contrast kinetics may be reduced, thereby reducing the number of patient rescans, which may improve the processor processing efficiency of the imaging system by reducing the number of images that have to be reconstructed, for example. A further technical effect of a scan prescription display panel as disclosed herein is that an operator of the imaging system may view the scan prescription as the operator is building the scan prescription via a simple and intuitive display panel, thus avoiding having the operator have to click through various menus, checkboxes, and text boxes to build the scan prescription while maintaining, in their head, the scan prescription as it is built. Doing so may reduce errors in the generation of the scan prescription, avoiding delays in initiating contrast scans and reducing the number of rescans.

The disclosure also provides support for a computing device comprising a display screen, the computing device being configured to display on the screen a scan interface in a prescription view, and further configured to receive user input via the scan interface in the prescription view to enable prescription of a contrast observation slice for tracking arrival of a contrast bolus during a contrast scan, and additionally being configured to display on the screen a scanning button that can be reached directly from the scan interface in the prescription view, wherein the scanning button is selectable to launch a live scanning view of the scan interface that enables live 2D images of the contrast observation slice to seen within the scan interface, the live scanning view further including a contrast tracking display panel that displays an auto-triggering button that is selectable to enable auto-triggering of post-contrast image acquisition and enable a contrast intensity plot determined from the live 2D images to be seen within the contrast tracking display panel. In a first example of the computing device, the computing device is configured to command initiation of live 2D scanning in response to selection of a live scanning button of the live scanning view, wherein the live 2D scanning comprises acquisition of first imaging data with a medical imaging apparatus and reconstruction of the first imaging data into the live 2D images. In a second example of the computing device, optionally including the first example, the computing device is further configured to display on the screen, via the live scanning view of the scan interface, an injection button that is selectable to trigger measurement of contrast intensity in a trigger region of interest (ROI) of the live 2D images and generation of the contrast intensity plot. In a third example of the computing device, optionally including one or both of the first and second examples, the computing device is configured to, responsive to selection of the auto-triggering button and selection of the injection button of the live scanning view, generate the contrast intensity plot by measuring the contrast intensity in the trigger ROI of each of the live 2D images acquired after the selection of the injection button and display the contrast intensity plot within the contrast tracking display panel. In a fourth example of the computing device, optionally including one or more or each of the first through third examples, the computing device is configured to command initiation of the post-contrast image acquisition in response to a contrast intensity level of the contrast intensity plot reaching a threshold intensity and without further user input, wherein the post-contrast image acquisition comprises acquisition of second imaging data with the medical imaging apparatus and reconstruction of the second imaging data into one or more post-contrast images. In a fifth example of the computing device, optionally including one or more or each of the first through fourth examples, the contrast tracking display panel further displays a back-up timer button that is selectable to enable commencement of a back-up timer responsive to selection of the injection button and enable a visualization of the back-up timer to be seen within the contrast tracking display panel, wherein the computing device is configured to command initiation of the post-contrast image acquisition in response to the back-up timer reaching a threshold duration. In a sixth example of the computing device, optionally including one or more or each of the first through fifth examples, the medical imaging apparatus comprises a magnetic resonance imaging (MRI) apparatus. In a seventh example of the computing device, optionally including one or more or each of the first through sixth examples, the live scanning view of the scan interface displays an image subtraction button that is selectable to enable an image subtraction operation to be performed on the live 2D images. In an eighth example of the computing device, optionally including one or more or each of the first through seventh examples, the live scanning view of the scan interface displays a saturation button that is selectable to enable a saturation operation to be performed on the live 2D images. In a ninth example of the computing device, optionally including one or more or each of the first through eighth examples, the live scanning view of the scan interface displays a contrast scan button that is selectable to trigger the post-contrast image acquisition. In a tenth example of the computing device, optionally including one or more or each of the first through ninth examples, the scan interface in the prescription view includes a scan prescription display panel that displays a scan prescription for at least the post-contrast image acquisition in a timeline format.

The disclosure also provides support for a method for a contrast scan, comprising: displaying, in a prescription view of a scan interface on a display device, a set of initial 2D images of an imaging subject, receiving, via the prescription view of the scan interface, user selection of a contrast observation slice and a trigger region of interest (ROI) on the contrast observation slice, displaying, in response to a first user input, a live scanning view of the scan interface that includes a viewport for displaying a live 2D image of the contrast observation slice and a contrast tracking display panel, updating the live 2D image in the viewport as new live 2D images are received, receiving a second user input indicating injection of a contrast agent to the imaging subject has begun, and responsive to the second user input, displaying, in the contrast tracking display panel, a live curve plotting measured contrast intensity of the trigger ROI as a function of time since the injection, while continuing to update the live 2D image of the contrast observation slice in the viewport, and commanding initiation of one or more post-contrast acquisitions responsive to any of the live curve reaching a threshold intensity, a third user input being received, and a back-up timer reaching a threshold duration. In a first example of the method, commanding initiation of the one or more post-contrast acquisitions responsive to any of the live curve reaching the threshold intensity, the third user input being received, and the back-up timer reaching the threshold duration comprises commanding initiation of the one or more post-contrast acquisitions responsive to whichever of the live curve reaching the threshold intensity, the third user input being received, and the back-up timer reaching the threshold duration occurs first in time. In a second example of the method, optionally including the first example, the method further comprises: displaying, via the prescription view of the scan interface, a scan prescription display panel including an editable timeline, setting a scan prescription for at least the one or more post-contrast acquisitions via user input to the editable timeline, displaying, via the live scanning view, a visualization of the scan prescription in the scan prescription display panel, and carrying out the one or more post-contrast acquisitions according to the scan prescription.

The disclosure also provides support for a system, comprising: a display device, one or more processors, and memory storing instructions executable by the one or more processors to: display, in a prescription view of a scan interface on the display device, a set of initial 2D images of an imaging subject, receive, via the prescription view of the scan interface, user selection of a contrast observation slice and a trigger region of interest (ROI) on the contrast observation slice, display, in response to a first user input and on the display device, a live scanning view of the scan interface that includes a viewport for displaying a live 2D image of the contrast observation slice and a contrast tracking display panel, update the live 2D image in the viewport as new live 2D images of the contrast observation slice are received, responsive to receiving a second user input indicating injection of a contrast agent to the imaging subject has begun, display, in the contrast tracking display panel, a live curve plotting measured contrast intensity of the trigger ROI as a function of time since the injection, while continuing to update the live 2D image of the contrast observation slice in the viewport, and command initiation of one or more post-contrast acquisitions responsive to any of the live curve reaching a threshold intensity, a third user input being received, and a back-up timer reaching a threshold duration. In a first example of the system, the instructions are executable to: responsive to receiving a fourth user input selecting an auto-triggering button of the scan interface and receiving a fifth user input selecting a back-up timer button of the scan interface, command initiation of the one or more post-contrast acquisitions responsive to the live curve reaching the threshold intensity unless the third user input is received before the live curve reaches the threshold intensity or unless the back-up timer reaches the threshold duration before the live curve reaches the threshold intensity. In a second example of the system, optionally including the first example, the instructions are executable to: responsive to not receiving the fourth user input selecting the auto-triggering button of the scan interface and receiving the fifth user input selecting the back-up timer button of the scan interface, command initiation of the one or more post-contrast acquisitions responsive to the third user input being received unless the back-up timer reaches the threshold duration before the third user input is received. In a third example of the system, optionally including one or both of the first and second examples, the system further comprises: a magnetic resonance imaging (MRI) scanner, and wherein the instructions are further executable to: command the MRI scanner to obtain the live 2D image and the new live 2D images of the contrast observation slice, and responsive to receiving a fourth user input, via the live scanning view, adjust the contrast observation slice to a new contrast observation slice, command the MRI scanner to obtain additional new live 2D images of the new contrast observation slice, and display the additional new live 2D images of the new contrast observation slice in the viewport. In a fourth example of the system, optionally including one or more or each of the first through third examples, the instructions are executable to acquire a baseline image and wherein the baseline image is subtracted from each live 2D image of the contrast observation slice in response to selection of an image subtraction button of the live scanning view of the scan interface. In a fifth example of the system, optionally including one or more or each of the first through fourth examples, the instructions are executable to acquire each live 2D image of the contrast observation slice with a saturation pulse sequence in response to selection of a saturation button of the live scanning view of the scan interface.

The disclosure also provides support for a computing device comprising a display screen, the computing device being configured to display on the screen a scan interface including a scan prescription display panel in a timeline view including an editable version of a timeline, the scan prescription display panel in the timeline view configured to receive user input to enable a scan prescription of a contrast scan of an imaging subject to be set while displaying each step of the scan prescription via the editable version of the timeline as that step is set, and additionally being configured to display on the screen a button that can be reached directly from the scan interface, wherein the button is selectable to initiate the contrast scan and launch a scanning view of the scan prescription display panel that enables each step of the scan prescription to be seen via the timeline as the contrast scan is carried out. In a first example of the computing device, the computing device is configured to save each step of the scan prescription and carry out the contrast scan according to the scan prescription. In a second example of the computing device, optionally including the first example, the scan prescription display panel in the timeline view includes an add mask button and an add phase button, and the computing device is configured to: add a mask step to the scan prescription and a mask tile to the timeline in response to user selection of the add mask button, add a first phase and a first delay to the scan prescription and a first phase tile and a first delay tile to the timeline in response to a first user selection of the add phase button, and add a second phase and a second delay to the scan prescription and a second phase tile and a second delay tile to the timeline in response to a second user selection of the add phase button. In a third example of the computing device, optionally including one or both of the first and second examples, the computing device is configured to adjust a duration of the first delay in response to user input to the first delay tile. In a fourth example of the computing device, optionally including one or more or each of the first through third examples, the timeline in the scanning view of the scan prescription display panel includes the mask tile, an injection tile, the first phase tile, the first delay tile, the second phase tile, and the second delay tile and further includes a time marker depicting time points from an end of an injection step depicted by the injection tile to a start of the first phase and the second phase, respectively. In a fifth example of the computing device, optionally including one or more or each of the first through fourth examples, the computing device is configured to adjust a visual appearance of the mask tile responsive to the mask step being initiated, and further adjust a visual appearance of the mask tile responsive to the mask step being completed. In a sixth example of the computing device, optionally including one or more or each of the first through fifth examples, the computing device is configured to display on the screen the scan interface in a prescription view, and further configured to receive user input via the scan interface in the prescription view to enable prescription of a contrast observation slice for tracking arrival of a contrast bolus during the contrast scan, and wherein the editable version of the timeline is displayed within the scan interface in the prescription view. In a seventh example of the computing device, optionally including one or more or each of the first through sixth examples, the computing device is additionally configured to display on the screen a live scanning button that can be reached directly from the scan interface, wherein the live scanning button is selectable to enable live 2D scanning of the contrast observation slice, and wherein the button is a scanning button that is also selectable to launch a live scanning view of the scan interface that enables live 2D images of the contrast observation slice to be seen within the scan interface, and wherein the scanning view of the scan prescription display panel is displayed within the live scanning view of the scan interface. In an eighth example of the computing device, optionally including one or more or each of the first through seventh examples, the live scanning view further includes a contrast tracking display panel that displays an auto-triggering button that is selectable to enable auto-triggering of post-contrast image acquisition and enable a contrast intensity plot determined from the live 2D images to be seen within the contrast tracking display panel.

The disclosure also provides support for a method for a contrast scan, comprising: displaying a timeline view of a scan prescription display panel on a display device, receiving a first user input to the scan prescription display panel, and in response, displaying an editable version of a timeline of a scan prescription for the contrast scan that includes a first tile corresponding to a first step of the scan prescription as selected via the first user input, adjusting the scan prescription via user input to the editable version of the timeline, and making a corresponding adjustment to the editable version of the timeline displayed on the display device, and receiving a command to initiate the contrast scan, and in response, displaying a scanning view of the scan prescription display panel on the display device and carrying out the contrast scan according to the scan prescription, wherein the scanning view of the scan prescription display panel includes the timeline with a tile for each step of the scan prescription arranged in temporal order. In a first example of the method, the method further comprises: receiving a user selection of a table button of the timeline view of the scan prescription display panel, and in response, switching from the timeline view to a table view of the scan prescription display panel, the table view including an editable table of the scan prescription. In a second example of the method, optionally including the first example, adjusting the scan prescription via user input to the editable version of the timeline comprises performing a first adjustment to the scan prescription via user input to the editable version of the timeline, and wherein the editable table of the scan prescription is populated with the first adjustment to the scan prescription. In a third example of the method, optionally including one or both of the first and second examples, the method further comprises: performing a second adjustment to the scan prescription via user input to the editable table. In a fourth example of the method, optionally including one or more or each of the first through third examples, displaying the timeline view of the scan prescription display panel on the display device comprises displaying the timeline view of the scan prescription display panel within a prescription view of a scan interface on the display device and wherein displaying the scanning view of the scan prescription display panel on the display device comprises displaying the scanning view of the scan prescription display panel within a live scanning view of the scan interface on the display device. In a fifth example of the method, optionally including one or more or each of the first through fourth examples, in the prescription view, the scan interface displays a set of initial 2D images of an imaging subject and is configured to receive user selection of a contrast observation slice and a trigger region of interest (ROI) on the contrast observation slice, wherein in the live scanning view, the scan interface includes a viewport for displaying a live 2D image of the contrast observation slice and a contrast tracking display panel, and the method further comprises: updating the live 2D image in the viewport as new live 2D images of the contrast observation slice are received, displaying, in the contrast tracking display panel, a live curve plotting measured contrast intensity of the trigger ROI as a function of time since an injection of contrast agent, while continuing to update the live 2D image of the contrast observation slice in the viewport, and commanding initiation of one or more post-contrast acquisitions responsive to any of the live curve reaching a threshold intensity, a user selection of start contrast button being received, and a back-up timer reaching a threshold duration.

The disclosure also provides support for a system, comprising: a display device, one or more processors, and memory storing instructions executable by the one or more processors to: display a timeline view of a scan prescription display panel on the display device, the timeline view including an editable version of a timeline of a scan prescription for a contrast scan that includes a first tile corresponding to a first step of the scan prescription, adjust the scan prescription via a user input to the editable version of the timeline, and make a corresponding adjustment to the editable version of the timeline displayed on the display device, and receive a command to initiate the contrast scan, and in response, display a scanning view of the scan prescription display panel on the display device and carry out the contrast scan according to the scan prescription, wherein the scanning view of the scan prescription display panel includes the timeline with a tile for each step of the scan prescription arranged in temporal order. In a first example of the system, adjusting the scan prescription via the user input to the editable version of the timeline, and making the corresponding adjustment to the editable version of the timeline displayed on the display device comprises adding a second step to the scan prescription in response to the user input and adding a second tile corresponding to the second step to the editable version of the timeline. In a second example of the system, optionally including the first example, the first tile includes a mask tile added to the editable version of the timeline in response to user selection of an add mask button and the user input comprises selection of an add phase button, wherein the first step of the scan prescription is a mask step and the second step of the scan prescription is a first post-contrast acquisition phase, and wherein the second tile is a first phase tile. In a third example of the system, optionally including one or both of the first and second examples, a delay tile is added to the editable version of the timeline along with the first phase tile, the delay tile including a delay duration editable via user input to the delay tile. In a fourth example of the system, optionally including one or more or each of the first through third examples, the instructions are further executable to, as the contrast scan is carried out, adjust a visual appearance of each tile of the timeline in the scanning view as each step of the scan prescription is carried out.

As used herein, the term "approximately" is construed to mean plus or minus five percent of the range unless otherwise specified.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A computing device comprising a display screen, the computing device being configured to display on the screen a scan interface in a prescription view, and further configured to receive user input via the scan interface in the prescription view to enable prescription of a contrast observation slice for tracking arrival of a contrast bolus during a contrast scan, and additionally being configured to display on the screen a scanning button that can be reached directly from the scan interface in the prescription view, wherein the scanning button is selectable to launch a live scanning view of the scan interface that enables live 2D images of the contrast observation slice to seen within the scan interface, the live scanning view further including a contrast tracking display panel that displays an auto-triggering button that is selectable to enable auto-triggering of post-contrast image acquisition and enable a contrast intensity plot determined from the live 2D images to be seen within the contrast tracking display panel.

2. The computing device of claim 1, wherein the computing device is configured to command initiation of live 2D scanning in response to selection of a live scanning button of the live scanning view, wherein the live 2D scanning comprises acquisition of first imaging data with a medical imaging apparatus and reconstruction of the first imaging data into the live 2D images.

3. The computing device of claim 2, wherein the computing device is further configured to display on the screen, via the live scanning view of the scan interface, an injection button that is selectable to trigger measurement of contrast intensity in a trigger region of interest (ROI) of the live 2D images and generation of the contrast intensity plot.

4. The computing device of claim 3, wherein the computing device is configured to, responsive to selection of the auto-triggering button and selection of the injection button of the live scanning view, generate the contrast intensity plot by measuring the contrast intensity in the trigger ROI of each of the live 2D images acquired after the selection of the injection button and display the contrast intensity plot within the contrast tracking display panel.

5. The computing device of claim 4, wherein the computing device is configured to command initiation of the post-contrast image acquisition in response to a contrast intensity level of the contrast intensity plot reaching a threshold intensity and without further user input, wherein the post-contrast image acquisition comprises acquisition of second imaging data with the medical imaging apparatus and reconstruction of the second imaging data into one or more post-contrast images.

6. The computing device of claim 5, wherein the contrast tracking display panel further displays a back-up timer button that is selectable to enable commencement of a back-up timer responsive to selection of the injection button and enable a visualization of the back-up timer to be seen within the contrast tracking display panel, wherein the computing device is configured to command initiation of the post-contrast image acquisition in response to the back-up timer reaching a threshold duration.

7. The computing device of claim 6, wherein the medical imaging apparatus comprises a magnetic resonance imaging (MRI) apparatus.

8. The computing device of claim 1, wherein the live scanning view of the scan interface displays an image subtraction button that is selectable to enable an image subtraction operation to be performed on the live 2D images.

9. The computing device of claim 1, wherein the live scanning view of the scan interface displays a saturation button that is selectable to enable a saturation operation to be performed on the live 2D images.

10. The computing device of claim 1, wherein the live scanning view of the scan interface displays a contrast scan button that is selectable to trigger the post-contrast image acquisition.

11. The computing device of claim 1, wherein the scan interface in the prescription view includes a scan prescription display panel that displays a scan prescription for at least the post-contrast image acquisition in a timeline format.

12. A method for a contrast scan, comprising:
displaying, in a prescription view of a scan interface on a display device, a set of initial 2D images of an imaging subject;
receiving, via the prescription view of the scan interface, user selection of a contrast observation slice and a trigger region of interest (ROI) on the contrast observation slice;
displaying, in response to a first user input, a live scanning view of the scan interface that includes a viewport for displaying a live 2D image of the contrast observation slice and a contrast tracking display panel;
updating the live 2D image in the viewport as new live 2D images are received;
receiving a second user input indicating injection of a contrast agent to the imaging subject has begun, and responsive to the second user input, displaying, in the contrast tracking display panel, a live curve plotting measured contrast intensity of the trigger ROI as a function of time since the injection, while continuing to update the live 2D image of the contrast observation slice in the viewport; and
commanding initiation of one or more post-contrast acquisitions responsive to any of the live curve reaching a threshold intensity, a third user input being received, and a back-up timer reaching a threshold duration.

13. The method of claim 12, wherein commanding initiation of the one or more post-contrast acquisitions responsive to any of the live curve reaching the threshold intensity, the third user input being received, and the back-up timer reaching the threshold duration comprises commanding initiation of the one or more post-contrast acquisitions responsive to whichever of the live curve reaching the threshold intensity, the third user input being received, and the back-up timer reaching the threshold duration occurs first in time.

14. The method of claim 12, further comprising:
displaying, via the prescription view of the scan interface, a scan prescription display panel including an editable timeline;
setting a scan prescription for at least the one or more post-contrast acquisitions via user input to the editable timeline;
displaying, via the live scanning view, a visualization of the scan prescription in the scan prescription display panel; and
carrying out the one or more post-contrast acquisitions according to the scan prescription.

15. A system, comprising:
a display device;
one or more processors; and
memory storing instructions executable by the one or more processors to:
display, in a prescription view of a scan interface on the display device, a set of initial 2D images of an imaging subject;
receive, via the prescription view of the scan interface, user selection of a contrast observation slice and a trigger region of interest (ROI) on the contrast observation slice;
display, in response to a first user input and on the display device, a live scanning view of the scan interface that includes a viewport for displaying a live 2D image of the contrast observation slice and a contrast tracking display panel;
update the live 2D image in the viewport as new live 2D images of the contrast observation slice are received;
responsive to receiving a second user input indicating injection of a contrast agent to the imaging subject has begun, display, in the contrast tracking display panel, a live curve plotting measured contrast intensity of the trigger ROI as a function of time since the injection, while continuing to update the live 2D image of the contrast observation slice in the viewport; and
command initiation of one or more post-contrast acquisitions responsive to any of the live curve reaching a threshold intensity, a third user input being received, and a back-up timer reaching a threshold duration.

16. The system of claim 15, wherein the instructions are executable to:
responsive to receiving a fourth user input selecting an auto-triggering button of the scan interface and receiving a fifth user input selecting a back-up timer button of the scan interface, command initiation of the one or more post-contrast acquisitions responsive to the live curve reaching the threshold intensity unless the third user input is received before the live curve reaches the threshold intensity or unless the back-up timer reaches the threshold duration before the live curve reaches the threshold intensity.

17. The system of claim 16, wherein the instructions are executable to:
responsive to not receiving the fourth user input selecting the auto-triggering button of the scan interface and receiving the fifth user input selecting the back-up timer button of the scan interface, command initiation of the one or more post-contrast acquisitions responsive to the third user input being received unless the back-up timer reaches the threshold duration before the third user input is received.

18. The system of claim 15, further comprising a magnetic resonance imaging (MRI) scanner, and wherein the instructions are further executable to:
command the MRI scanner to obtain the live 2D image and the new live 2D images of the contrast observation slice; and
responsive to receiving a fourth user input, via the live scanning view, adjust the contrast observation slice to a new contrast observation slice, command the MRI scanner to obtain additional new live 2D images of the new contrast observation slice, and display the additional new live 2D images of the new contrast observation slice in the viewport.

19. The system of claim 15, wherein the instructions are executable to acquire a baseline image and wherein the baseline image is subtracted from each live 2D image of the contrast observation slice in response to selection of an image subtraction button of the live scanning view of the scan interface.

20. The system of claim 15, wherein the instructions are executable to acquire each live 2D image of the contrast observation slice with a saturation pulse sequence in response to selection of a saturation button of the live scanning view of the scan interface.

* * * * *